United States Patent
Tsunoda et al.

(10) Patent No.: US 9,708,603 B2
(45) Date of Patent: Jul. 18, 2017

(54) METHOD FOR AMPLIFYING CDNA DERIVED FROM TRACE AMOUNT OF SAMPLE

(71) Applicant: HITACHI, LTD., Tokyo (JP)

(72) Inventors: Hiroyuki Tsunoda, Tokyo (JP); Huan Huang, Tokyo (JP); Mari Ohta, Tokyo (JP); Hideki Kambara, Tokyo (JP)

(73) Assignee: HITACHI, LTD., Tokyo (JP)

( * ) Notice: Subject to any disclaimer, the term of this patent is extended or adjusted under 35 U.S.C. 154(b) by 326 days.

(21) Appl. No.: 14/383,209

(22) PCT Filed: Nov. 21, 2012

(86) PCT No.: PCT/JP2012/080141
§ 371 (c)(1),
(2) Date: Sep. 5, 2014

(87) PCT Pub. No.: WO2013/145431
PCT Pub. Date: Oct. 3, 2013

(65) Prior Publication Data
US 2015/0024959 A1  Jan. 22, 2015

(30) Foreign Application Priority Data

Mar. 30, 2012 (JP) .................................. 2012-078675

(51) Int. Cl.
C12N 15/10 (2006.01)
C12Q 1/68 (2006.01)
(52) U.S. Cl.
CPC ..... *C12N 15/1096* (2013.01); *C12N 15/1065* (2013.01); *C12Q 1/686* (2013.01); *C12Q 1/6844* (2013.01)
(58) Field of Classification Search
None
See application file for complete search history.

(56) References Cited

U.S. PATENT DOCUMENTS

2003/0148276 A1* 8/2003 Li ................ C12Q 1/6809
435/6.12
2007/0281313 A1 12/2007 Taniguchi et al.
(Continued)

FOREIGN PATENT DOCUMENTS

JP 2007-319028 A 12/2007
WO 2006/085616 A1 8/2006

OTHER PUBLICATIONS

Brady et al. Representative in vitro cDNA amplification from individual hemopoietic cells and colonies. Methods in Molecular and Cellular Biology 2:17-25 (1990).*
(Continued)

*Primary Examiner* — Samuel Woolwine
(74) *Attorney, Agent, or Firm* — Baker Botts L.L.P.

(57) ABSTRACT

The problem to be solved by the present invention is to provide a method for preparing a sample for comprehensively and accurately analyzing gene expression in a single cell or a few cells, for example, by a large-scale DNA sequencer. The present invention relates to a method for amplifying cDNA from mRNA in a cell, comprising: (1) capturing mRNA derived from the cell by a first DNA probe containing a first tag sequence and a poly T sequence and being immobilized to a solid carrier in a single reaction vessel, and synthesizing a first strand cDNA from the mRNA by a reverse transcription reaction; (2) removing a reaction reagent from the reaction vessel while keeping the first strand cDNA synthesized onto the solid carrier in the reaction vessel; (3) adding a polynucleotide sequence consisting of one type of nucleotides to 3' terminal of the first strand cDNA on the solid carrier; (4) hybridizing a second DNA probe containing a second tag sequence and a complementary sequence to the polynucleotide sequence with the cDNA to which the polynucleotide sequence is added, and synthesizing a second strand cDNA; and (5) performing a (Continued)

DNA amplification reaction using the second strand cDNA synthesized on the solid carrier as a template.

16 Claims, 9 Drawing Sheets

(56) References Cited

U.S. PATENT DOCUMENTS

2009/0291852 A1    11/2009  Saitou et al.
2013/0116130 A1*   5/2013   Fu ..................... C12Q 1/6837
                                                         506/4

OTHER PUBLICATIONS

Brady & Iscove. Construction of cDNA libraries from single cells. Methods in Enzymology 225:611-623 (1993).*
Iscove et al. Representation is faithfully preserved in global cDNA amplified exponentially from sub-picogram quantities of mRNA. Nature Biotechnology 20:940-943 (2002).*
Lambert & Williamson. cDNA library construction from small amounts of RNA using paramagnetic beads and PCR. Nucleic Acids Research 21(3):775-776 (1993).*
Lambert & Williamson. cDNA library construction using streptavidin-paramagnetic beads and PCR. From: The Nucleic Acid Protocols Handbook, edited by R. Rapley. Humana Press Inc., Totowa, NJ. Chapter 41, pp. 289-294 (2000).*
Schmidt & Mueller. Controlled ribonucleotide tailing of cDNA ends (CRTC) by terminal deoxynucleotidyl transferase: a new approach in PCR-mediated analysis of mRNA sequences. Nucleic Acids Research 24(9):1789-1791 (1996).*
Shepard & Cooper. PCR synthesis of cDNA from total RNA. Biotechniques 23(2):202-204 (1997).*
Verlinsky et al. Isolation of cDNA libraries from individual human preimplantation embryos. Molecular Human Reproduction 4(6): 571-575 (1998).*
Wang & Jones. cDNA generation on paramagnetic beads. From: Methods in Molecular Biology, vol. 221: Generation of cDNA Libraries: Methods and Protocols, edited by S.-Y. Ying. Humana Press Inc., Totowa, NJ. Chapter 3, pp. 25-31 (2003).*
Kurimoto et al. An improved single-cell cDNA amplification method for efficient high-density oligonucleotide microarray analysis. Nucleic Acids Research 34(5):e42 (5 pages), Mar. 17, 2006.*
Fuchou Tang et al., RNA-Seq analysis to capture the transcriptome landscape of a single cell, Nature Protocols 2010, pp. 516-535, vol. 5, No. 3.
Kiyomi Taniguchi et al., Quantitative analysis of gene expression in a single cell by qPCR, Nature Methods, Jul. 2009, pp. 503-506, vol. 6, No. 7.
Teemu Kivioji et al., Counting absolute numbers of molecules using unique molecular identifiers, Nature Methods, Jan. 2012, pp. 72-74, vol. 9, No. 1.
Kazuki Kurimoto et al., An improved single-cell cDNA amplification method for efficient high-density oligonucleotide microarray analysis, Nucleic Acids Research, 2006, pp. 1-17, vol. 34, No. 5 e42.
Kazuki Kurimoto et al., Global single-cell cDNA amplification to proivde a template for representative high-density oligonucleotide microarray analysis, Nature Protocols, 2007, pp. 739-752, vol. 2, No. 3.
Fuchou Tang et al., mRNA-Seq whole-transcriptome analysis of a single cell, Nature Methods, May 2009, pp. 377-382 vol. 6, No. 5.
Fuchou Tang et al., Tracing the Derivation of Embryonic Stem Cells from the Inner Cell Mass by single-Cell RNA-Seq Analysis, Cell Stem Cell 6, May 7, 2010, pp. 468-478.

* cited by examiner

METHOD FOR AMPLIFYING CDNA DERIVED FROM TRACE AMOUNT OF SAMPLE

BACKGROUND OF THE INVENTION

Field of the Invention

The present invention relates to analysis of a trace amount of nucleic acid component such as RNA or DNA contained in one or a few cells, and particularly relates to a method of producing cDNA from mRNA and equally amplifying cDNA.

Background Art

Gene expression analysis has been widely used as a means for accurately elucidating the state of a living body. As a typical expression analysis method, a real-time PCR method and a micro-array method have been known. For the analysis, mRNA is extracted from various samples and put in use. For example, mRNA extracted from cultured and proliferated cells or mRNA extracted from a tissue piece containing a plurality of cells has been frequently used. An amount of each mRNA measured is regarded as an average amount of mRNA molecules collected from a plurality of cells and to be subjected to analysis.

In the meantime, a significant development has been recently made in the academic field. In a tissue piece and a cell population, which are up to present regarded as a group of homogeneous cells and collected, it has been found that a plurality types of cells are present. For example, a cancer tissue contains a cancer stem cell, from which cancer is originated. It has been elucidated that cancer cells are supplied from the cancer stem cell. Furthermore, in embryonic stem (ES) cells application of which to regenerative medicine has been expected, it has been elucidated that individual cells of the ES cell population are not homogeneous and that cells having a different differentiation potency are present in the population. In the studies dealing with cells whose characteristics differ from each other, a conventional method which analyzes an expression based on the average expression of a cell population is no longer sufficient. There is a possibility that true expression analysis could not be made unless genes of individual cells are analyzed at the single-cell level.

However, the amount of mRNA contained in a single cell is extremely small. The amount of mRNA contained in a cultured human cell is presumably about 2 pg or less. It is difficult to analyze expression of a trace amount of mRNA by a conventional method. In the circumstances, to realize the expression analysis of a trace amount of mRNA derived from a single cell, various approaches have been developed.

As a method for a quantitative gene expression analysis, a real-time PCR method is excellent. The present inventors have already reported on the method for analyzing the amount of mRNA derived from a single cell by a real-time PCR method. More specifically, in the method we developed, mRNA is extracted from a single cell and a cDNA library is constructed on magnetic beads and used as a sample for real time PCR (Patent Document 1 and Non Patent Document 1). In the method, amplification is performed by use of different real-time PCR primers between genes and compared to a calibration curve of a standard sample amplified by the same primer. In this manner, accurate quantitative analysis can be realized. In this method, however, since the number of genes simultaneously measured is limited to several, it was difficult to make comprehensive expression analysis.

In contrast, as a method for a comprehensive gene expression analysis, a micro-array method is excellent. Kurimoto et al., have realized comprehensive expression analysis of a single cell in combination with a global amplification method (Patent Document 2, Non Patent Documents 2 and 3). However, the micro-array method may be inferior in quantitative performance, since the intensity of expression is measured based on hybridization of a gene-sequence specific probe compartmentally arranged on a chip, with a sample nucleic acid.

The real-time PCR method and the micro-array method have a following common problem: a sample the nucleotide sequence of which has not been determined, cannot be analyzed. In a cell, various unknown variant mRNA molecules and many unknown non-coding RNA molecules involved in gene expression regulation although they do not encode proteins, are present. Importance of expression analysis of these unknown RNA molecules in elucidating life has been extremely increased in recent years.

Under such circumstances, large-scale DNA sequencers have been recently developed. With this development, a novel method, that is, an expression analysis method (RNA-Seq), has been attracted attention, in which the sequence analysis of mRNA is made based on the analysis of cDNA produced from the mRNA by a DNA sequencer. RNA-Seq is capable of simultaneously analyzing nucleotide sequences of tens of millions to several hundred-millions of DNA fragments. The sequences thus analyzed are subjected to a mapping operation using a known gene sequence, with a computer. The number of fragments whose sequences are mapped is counted to computationally obtain the expression amount of RNA.

In RNA-Seq, expression of unknown mRNA can be analyzed as long as a reference genomic DNA sequence for use in mapping is known. Thus, RNA-Seq has a great advantage in overcoming drawbacks of conventional expression analysis methods. Furthermore, the dynamic range of measurement is as wide as 5 log. Thus, it is considered that all mRNA molecules expressed in a cell can be quantitatively measured at a time. Moreover, in RNA-Seq, expression amounts of genes are not simply compared but the sequences thereof can be analyzed, with the result that information, such as a mutation of gene itself, can be obtained other than that obtained by quantitative analysis. Therefore, RNA-Seq has a large impact on the field of bioscience as an innovative analysis method.

As described above, RNA-Seq by a large-scale DNA sequencer is an extremely excellent analysis method; however, assuming that expression of a single cell is analyzed by the sequencer, there is a large problem that is to be overcome. This is a process of amplifying DNA, which is essential since a large-scale sequencer requires a large amount of DNA as an analysis sample. For example, in preparing samples for a SOLiD sequencer (Lifetech Co., Ltd.), a step of individual amplification by emulsion PCR is required. Before the step, it is necessary to amplify a DNA sample up to approximately several hundreds of ng. In this amplification process, several steps are required for preparing a sample so as to satisfy the specifications defined by a sequencer, such as addition of an amplification adaptor and size selection based on DNA fragment length. Because of this, it is very difficult to actually amplify DNA up to several hundreds of ng so as to satisfy the specifications defined by a large-scale sequencer based on a trace amount of mRNA derived from a single cell. Even if amplification can be made, amplification does not equally proceed during amplification. As a result, there is a high possibility that the obtained sample fails to reflect the expression amount ratio of mRNA molecules in a single cell.

Kits for preparing a sample for RNA-Seq so as to satisfy the specifications defined by individual sequencers are available from various manufacturers; however, none of the kits fail to prepare a sample from a single cell-level mRNA of 2 pg or less. Accordingly, in order to perform RNA-Seq of a single cell, it is necessary to develop an original method for preparing a sample. Such a method has been reported in some papers.

For example, Tang et al. improved the aforementioned global amplification method and succeeded in expression analysis in single-cell such as an ovum or an ES cell of a mouse by using a large-scale sequencer (Non Patent Documents 4 and 5). The global amplification method includes the following steps:

(1) extracting mRNA from a single cell and synthesizing cDNA by use of DNA primer (UP1) having a poly T sequence and a tag sequence for PCR amplification; (2) degrading the remaining unreacted DNA primer in cDNA synthesis, with single-strand DNA degradation enzyme, i.e., exonuclease I; (3) inactivating exonuclease I with heat, and then degrading mRNA with RNaseH and adding a poly A sequence to the 3' terminal of cDNA with TdT (Terminal Deoxynucleotidyl Transferase); (4) performing synthesis reaction of a double-strand by use of a DNA primer (UP2) having a tag sequence for amplification, which is different from that of the UP1 primer as mentioned above, and a poly T sequence; and (5) performing PCR amplification using the double-stranded DNA synthesized as a template, with a set of UP1 primer and UP2 primer.

This method is suitable for amplification of a trace amount of sample. Generally, if such a method is used, a serious problem, unequal amplification, may be accompanied. Unequal amplification refers to a phenomenon where the amplification rates of individual genes vary in a step of amplifying the genes, as previously described, with the result that the obtained results do not reflect the expression amount ratio of intracellular mRNA molecules. In other words, this is referred to as an amplification bias, which is going to be a significant problem in quantitatively comparing gene expression amounts.

The gene expression amount found in elucidating development and differentiation greatly varies depending upon the stage. Thus, if several-fold amplification bias is present, no significant problem occurs in some cases. However, if a marker is searched in the field of medicine where a further development is expected, there is a case where genes are desired to be distinguished even if the expression amounts of them differ only about twofold. In such a case, it is difficult to distinguish such small difference in expression amount between the genes by the expression analysis method giving a several-fold amplification bias. Because of this, it has been desired to develop a method directed to a single-cell mRNA for preparing a sufficient amount of sample for a large-scale sequencer and providing less amplification bias as much as possible.

PRIOR ART DOCUMENTS

Patent Documents

Patent Document 1: JP Patent Publication No. 2007-319028 A
Patent Document 2: WO 2006/085616

Non-Patent Documents

Non Patent Document 1: Taniguchi et al., Nature Methods 6, 503-506 (2009)
Non Patent Document 2: Kurimoto et al., Nucleic Acids Research 34, e42 (2006)
Non Patent Document 3: Kurimoto et al., Nature Protocol 2, 739-752 (2007)
Non Patent Document 4: Tang et al., Nature Methods 6, 377-382 (2009)
Non Patent Document 5: Tang et al., Cell Stem Cell 6, 468-478 (2010)

SUMMARY OF INVENTION

Technical Problem

A problem to be solved by the present invention is to provide a method for preparing a sample for comprehensively and accurately analyzing gene expression in a single cell or a few cells, for example, by a large-scale DNA sequencer. To attain this, it is necessary to efficiently convert a trace amount (several pg) of mRNA contained in a single cell into cDNA and amplify cDNA up to a sufficient amount (several hundreds of ng) satisfying the specifications defined by a large-scale sequencer. In addition, at the time of amplification, it is necessary to perform amplification without bias as much as possible so as not to change the expression amount ratio of mRNA molecules contained in the original cell. Since the amount of mRNA in a single cell is extremely low, the sample loss due to adsorption to a vessel wall and a pipette should be reduced as much as possible to enhance amplification efficiency. Then, if all sample preparation steps are performed in the same vessel, it is expected to suppress sample loss to a minimum. However, in this case, conversely, unreacted reagents and reaction by-products in individual steps are accumulated in the vessel, lowering efficiency and accuracy of the following reaction step. According to the present invention, it is an object to provide a method for amplifying a sufficient amount of sample with less bias from one or a few cells, as a sample for e.g., a large-scale DNA sequencing by preventing the aforementioned contradicted phenomena.

Solution to Problem

The present inventors have conducted intensive studies on a step of synthesizing cDNA from mRNA and the following step of amplifying cDNA, with the view to overcoming the aforementioned problems. As a result, we have elucidated a cause of reducing efficiency of amplification reaction and a cause of generating bias during amplification. Then, we have successfully conceived a series of steps from preparation to amplification of cDNA having a high amplification efficiency and less amplification bias, by overcoming these problems. As a result, we have developed a technique enabling a single cell gene expression analysis, for example, by a large-scale DNA sequencer.

More specifically, the present invention encompasses the followings:

[1] A method for amplifying cDNA from mRNA in a cell, comprising:

(1) capturing mRNA derived from the cell by a first DNA probe containing a first tag sequence and a poly T sequence and being immobilized to a solid carrier in a single reaction vessel, and synthesizing a first strand cDNA from the mRNA by a reverse transcription reaction;

(2) removing a reaction reagent from the reaction vessel while keeping the first strand cDNA synthesized onto the solid carrier in the reaction vessel;

(3) adding a polynucleotide sequence consisting of one type of nucleotides to 3' terminal of the first strand cDNA on the solid carrier;

(4) hybridizing a second DNA probe containing a second tag sequence and a complementary sequence to the polynucleotide sequence with the cDNA to which the polynucleotide sequence is added, and synthesizing a second strand cDNA; and (5) performing a DNA amplification reaction using the second strand cDNA synthesized on the solid carrier as a template.

[1-2] The method according to [1], wherein the cell is one or a few cells.

[2] The method according to [1], wherein the solid carrier is a magnetic bead.

[3] The method according to [1] or [2], wherein, in step (1), the first DNA probe is used in an amount of $4 \times 10^3$ molecules or less per solid carrier.

[4] The method according to any one of [1] to [3], wherein, in step (1), the first DNA probe is used in an amount of more than $2 \times 10^3$ molecules and $10^5$ molecules or less per solid carrier.

[5] The method according to [1] or [2], wherein, in step (1), the first DNA probe is a group of probes containing a two-nucleotide random sequence at the 3' terminal following the first tag sequence and the poly T sequence, and the first DNA probe is used in an amount of $10^4$ molecules or more per solid carrier.

[5-2] The method according to [5], wherein the random sequence is VN (V represents A or G or C, and N represents A or G or C or T).

[6] The method according to any one of [1] to [5], wherein, in step (2), the reaction reagent to be removed includes a reverse transcriptase.

[7] The method according to any one of [1] to [6], comprising no degradation and removal step of the first DNA probe by a DNase reaction.

[8] The method according to any one of [1] to [7], wherein, in step (3), the nucleotides are adenines (A).

[9] The method according to any one of [1] to [8], further comprising removing the reaction reagent after the polynucleotide sequence addition reaction of step (3).

[10] The method according to any one of [1] to [9], wherein, in step (4), the second DNA probe is a group of probes containing a two-nucleotide random sequence at the 3' terminal following the second tag sequence and the complementary sequence to the polynucleotide sequence.

[10-2] The method according to [10], wherein the random sequence is VN (V represents A or G or C, and N represents A or G or C or T).

[11] The method according to any one of [1] to [10], wherein, in step (5), the DNA amplification reaction is performed by using the first tag sequence present at the end of the second strand cDNA synthesized on the solid carrier, or the first tag sequence and the second tag sequence.

[11-2] The method according to any one of [1] to [11], wherein, in step (5), the DNA amplification reactions using a plurality of second strand cDNA synthesized on the solid carrier as templates are simultaneously performed.

[11-3] The method according to any one of [1] to [11], wherein, in step (5), the DNA amplification reaction is performed by using a primer containing at least the first tag sequence, or the primer containing at least the first tag sequence and a primer containing at least the second tag sequence.

[12] The method according to any one of [1] to [11], wherein, in step (5), the number of amplification reaction cycles is limited to the number or less at which exponential amplification is maintained.

[13] The method according to any one of [1] to [12], further comprising separating and removing DNA products of 200 bp or less from amplified DNA products by a method for separating and purifying the DNA products based on adsorption of DNA to beads.

[14] The method according to any one of [1] to [13], wherein the DNA amplification reaction is performed by repeatedly using the solid carrier to which the first strand DNA is immobilized.

[14-2] The method according to any one of [1] to [14], further comprising measuring RNA having no poly A sequence at the 3' terminal in the remaining solution from which mRNA is already captured by the solid carrier, in step (1).

[14-3] The method according to any one of [1] to [14], wherein the surface of the solid carrier is coated with a protein adsorption-preventing agent.

[15] The method according to any one of [1] to [14], further comprising allowing the solid carrier to stand still in a fresh buffer solution, after the reaction reagent is removed, in step (2).

[16] A method for determining the amount of mRNA in a cell, comprising determining the amount of mRNA in a cell based on the amount of DNA product amplified by the method according to any one of [1] to [14].

[17] A kit for amplifying cDNA from mRNA in a cell, comprising:

a solid carrier to which a first DNA probe containing a first tag sequence and a poly T sequence is immobilized, a means for adding a polynucleotide sequence consisting of one type of nucleotides to the 3' terminal of a cDNA sequence, a second DNA probe containing a second tag sequence and a complementary sequence to the polynucleotide sequence, and a primer containing at least the first tag sequence or a primer containing at least the first tag sequence and a primer containing at least the second tag sequence.

[17-2] The kit according to [17], wherein the solid carrier is a magnetic bead.

[17-3] The kit according to [17], wherein the first DNA probe is immobilized in an amount of $4 \times 10^3$ molecules or less per solid carrier.

[17-4] The kit according to [17], wherein the first DNA probe is immobilized in an amount of more than $2 \times 10^3$ molecules to $10^5$ molecules or less per solid carrier.

[17-5] The kit according to [17], wherein the one type of nucleotides are adenines (A).

[17-6] The kit according to [17], wherein the means for adding a polynucleotide sequence is terminal deoxynucleotidyl transferase (TdT).

[17-7] The kit according to [17], wherein the second DNA probe is a group of probes containing a two-nucleotide random sequence at the 3' terminal following the second tag sequence and the complementary sequence to the polynucleotide sequence.

[17-8] The kit according to [17], wherein the random sequence is VN (V represents A or G or C, and N represents A or G or C or T).

[17-9] The kit according to [17], further comprising a reverse transcriptase and a DNA polymerase.

[17-10] The kit according to [17], wherein the first DNA probe is a group of probes containing a two-nucleotide random sequence at the 3' terminal following the first tag sequence and the poly T sequence.

[17-11] The kit according to [17], wherein the random sequence is VN (V represents A or G or C, and N represents A or G or C or T).

Effect of the Invention

According to the method and kit of the present invention, it is possible to amplify a sufficient amount of sample for a large-scale DNA sequencing with less bias from one or a few cells. According to the present invention, gene expression analysis at a single cell level can be attained. Providing new life information to bioscience and the field of medicine in this manner is a great contribution. If behavior of cells as a population is understood not based on understanding of the properties in average as ever but based on understanding of properties of individual cells, and if responsiveness of cells to drugs and properties of cells are evaluated, the technique provided herein will find an extremely wider range of application than ever.

The present specification incorporates the contents described in the specification and/or the drawings of the Japanese Patent Application No. 2012-078675 based on which the present application claims priority.

The problems, constitutions and effects other than those described above will be apparently understood from the description of the following embodiments.

BRIEF DESCRIPTION OF THE DRAWINGS

FIG. 2A shows the measurement results of the amount of EEF1G gene present on magnetic beads during reverse transcription, by a quantitative PCR method. FIG. 2B shows the amount of EEF1G gene present in the amplified product up to the 2nd PCR. The number of molecules shown in the figure represents the number of immobilized UP1 probes per magnetic bead.

DETAILED DESCRIPTION OF THE INVENTION

The present invention will be more specifically described below.

Figure 1:
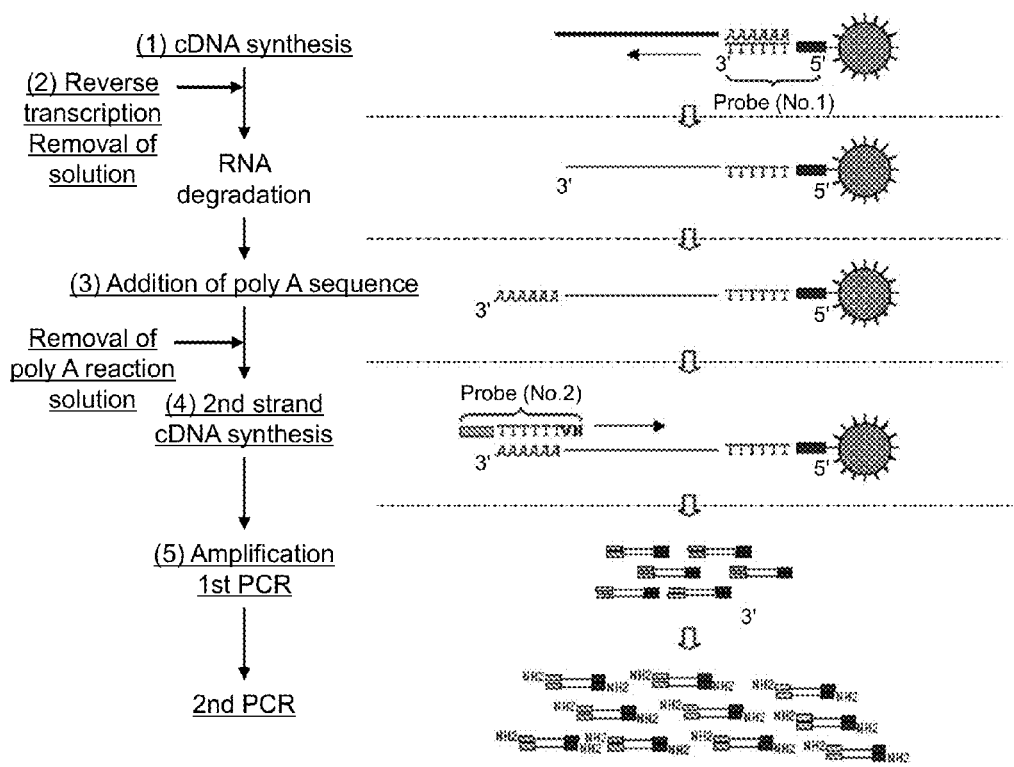
FIG. 1 is a chart schematically showing the steps of the protocol of the present invention.

Five steps of the method according to the present invention, for preparing a sample for a large-scale sequencer capable of attaining a single-cell gene expression analysis, will be described (FIG. 1).

(1) cDNA synthesis: a step of capturing mRNA by a first DNA probe (No. 1) containing a first tag sequence and a poly T sequence and being immobilized to a solid carrier and performing a reaction of synthesizing cDNA from the mRNA by a reverse transcription reaction in a single reaction vessel;

(2) Removal of reverse transcription reaction solution: a step of removing a reaction reagent from the reaction vessel while keeping a first strand cDNA synthesized on the solid carrier in the reaction vessel;

(3) Addition of poly A sequence (addition of a polynucleotide sequence with one type of nucleotides): a step of adding a poly A sequence (polynucleotide sequence consisting of one type of nucleotides) to the 3' terminal of the first strand cDNA on the solid carrier;

(4) Synthesis of a second strand cDNA (2nd strand cDNA): a step of hybridizing a second DNA probe (No. 2) containing a second tag sequence and a poly T sequence (a complementary sequence to the polynucleotide sequence) with cDNA having poly A sequence (polynucleotide sequence with one type of nucleotides) added thereto, and synthesizing a second strand cDNA;

(5) Amplification: a step of performing a DNA amplification reaction using the second strand cDNA synthesized on the solid carrier as a template.

Now, points of the present invention will be more specifically described below, step by step.

Figure 2:
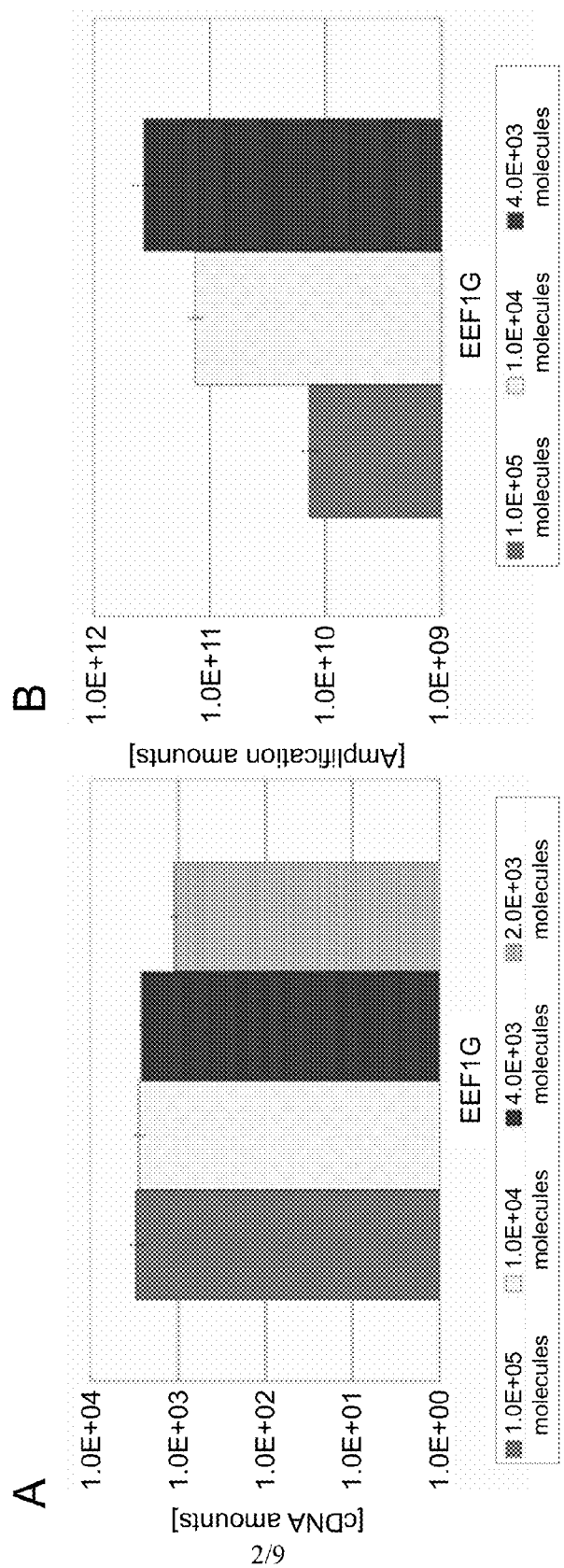
FIG. 2 is a graph showing the results of an experiment performed in order to check an optimal amount of probe to be immobilized to magnetic beads.

In step (1) of cDNA synthesis, magnetic beads may be used as the solid carrier. In view of efficiency of subsequent reactions (described later), optimizing the number of magnetic beads to be used in a single reaction and optimizing the amount of DNA probe to be immobilized to magnetic beads are important points in this step. More specifically, the number of magnetic beads to be used in a single reaction is preferably $10^6$ to $10^8$, and more preferably $10^7$. At this time, an appropriate amount of DNA probe to be immobilized to magnetic beads may be estimated (FIG. 2). In view of efficiency in a reverse transcription reaction, DNA probes of more than about $2\times10^3$ molecules to $10^5$ molecules per magnetic bead, preferably $3\times10^3$ molecules to $10^5$ molecules, more preferably $4\times10^3$ molecules to $10^5$ molecules may be desirably immobilized. In contrast, in view of efficiency of a PCR amplification reaction (described later), an immobilization amount of about $4\times10^3$ molecules or less may be preferable since not only amplification efficiency of PCR amplification is high but also an amplified artifact product is less obtained. Accordingly, the immobilization amount of DNA probe suitable for both reverse transcription and PCR amplification is more than $2\times10^3$ molecules to $4\times10^3$ molecules per magnetic bead, preferably $3\times10^3$ molecules to $4\times10^3$ molecules, and more preferably $4\times10^3$ molecules.

Figure 9:
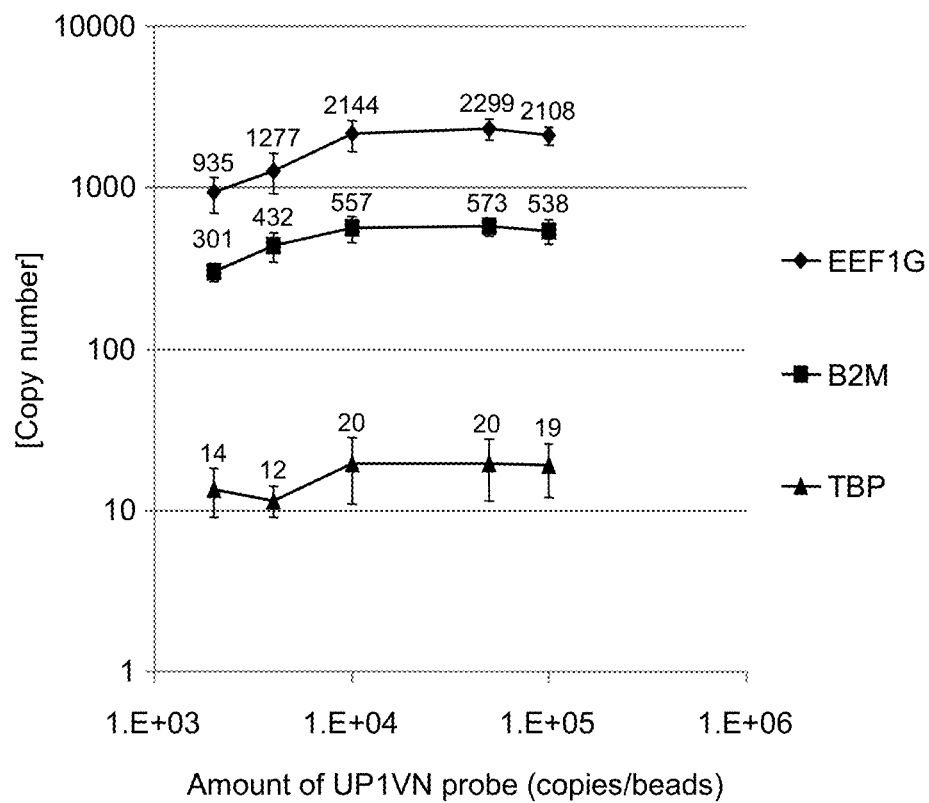
FIG. 9 is a graph showing the results of an experiment performed to check the amount of DNA probe having an optimal VN sequence to be immobilized to magnetic beads.

If a sequence such as a VN sequence having an effect of specifying the reverse transcription initiation point at the initiation point of a poly A sequence of mRNA is introduced to the 3' terminal of the first DNA probe to be immobilized to magnetic beads, it is expected to have an effect of reducing an artifact by-product which is produced by binding a plurality of probes to the poly A sequence. In this case, the optimal amount of probe to be immobilized to magnetic beads may vary. In view of reverse transcription efficiency, $10^4$ molecules or more per magnetic bead may be desirable (FIG. 9).

After completion of this step, cDNA having sequence information derived from a trace amount of mRNA of one or a few cells can be immobilized onto the magnetic bead carrier (cDNA library). In the subsequent steps, it is possible to prevent loss of trace amount of nucleic acid sample due to adsorption to a reaction vessel and a pipette.

Figure 3:
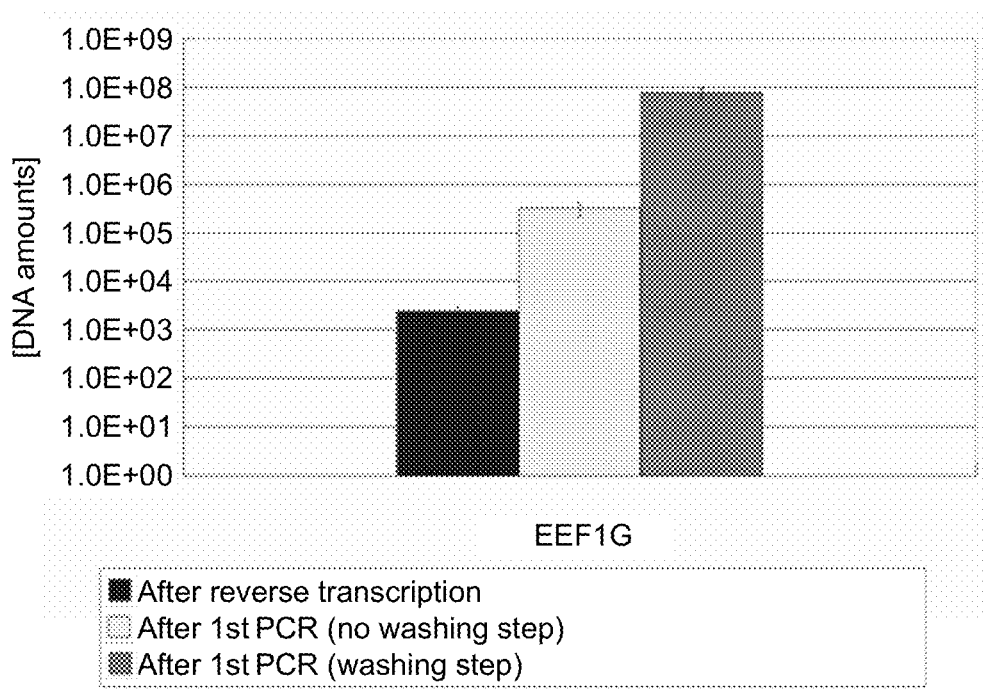
FIG. 3 is a graph showing the removal/washing effect of a reverse transcription reaction solution.

In step (2) of removing a reverse transcription reaction solution, the reaction solution used in reverse transcription is removed while magnetically separating magnetic beads, and magnetic beads are washed. A purpose of the washing operation is to prevent carryover of the reverse transcription solution containing a reverse transcriptase to the following step, thereby preventing reaction inhibition. This is the most important point in this step. If the washing operation for removing a reverse transcription reaction solution is not performed, amplification amount in 1st PCR drastically decreases, as is apparent from the experiments of the present inventors (FIG. 3). In addition, we investigated factors actually involved in reaction inhibition. As a result, it was confirmed that a reverse transcriptase, i.e., Superscript III, has a possibility of inhibiting poly A addition reaction performed in the following step.

In contrast, in the global amplification method performed by Tang et al. (Non Patent Documents 4 and 5), a next poly A addition reaction is performed in a solution without immobilizing cDNA. In this case, in order to prevent carryover of an unreacted primer in the previous step to the following step, the unreacted primer may be degraded by exonuclease I. Without the degradation step, a poly A sequence may be added also to the 3' terminal of the unreacted primer carried over, and used as a template in the following DNA amplification reaction, with the result that the amplification efficiency of a desired product significantly decreases. The treatment with exonuclease I to degrade such extra DNA is a method that has so far been generally and widely used.

Figure 4:
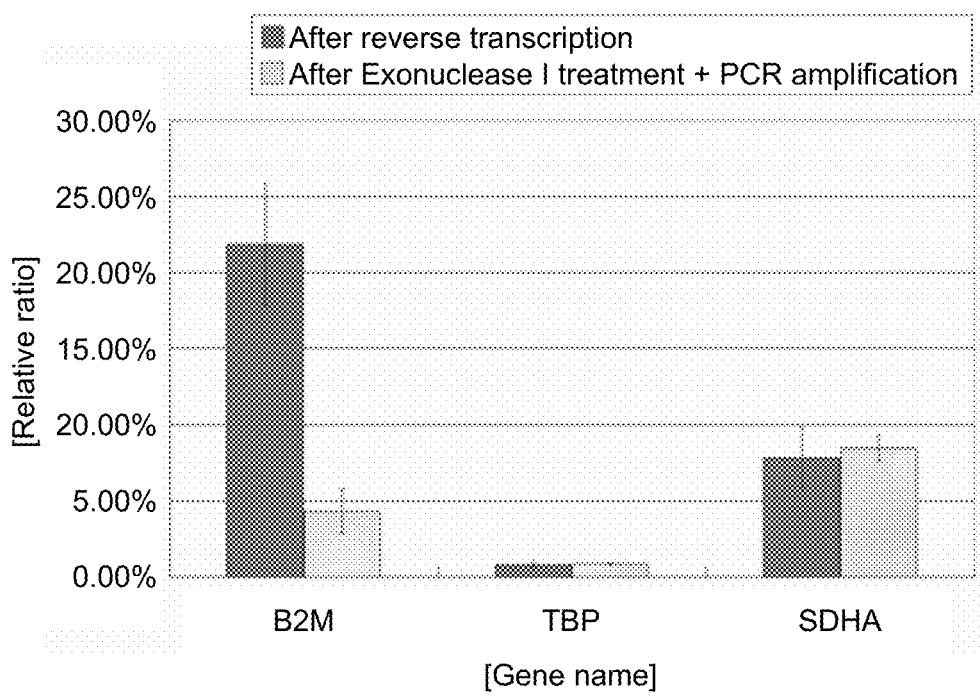
FIG. 4 is a graph showing the effect of treatment with exonuclease I on 1st PCR. The abscissa axis indicates the name of genes, amplification amounts of which were measured by quantitative PCR. The vertical axis indicates the relative value of amplification amount of each of the genes, which is calculated based on the amplification amount of EEF1G gene measured in the same experiment regarded as 100%.

However, our experiments showed that PCR amplification efficiency is greatly varied depending upon the type of gene by performing a treatment with exonuclease I, and amplification bias occurs (FIG. 4). In the example shown in FIG. 4, B2M gene corresponds to the case. It was found that the PCR amplification amount of B2M gene relatively reduces compared to those of other genes when B2M gene is treated with exonuclease I.

As a cause, it is expected that a cDNA sequence is partly degraded with exonuclease I. Since exonuclease I specifically degrades single-stranded DNA, double-stranded cDNA, i.e., an mRNA/cDNA hybrid obtained after cDNA synthesis, may not be degraded. However, if a single-strand structure is partially present in a certain type of gene sequence, exonuclease I may target the single-strand structure and degrade cDNA.

According to the protocol of the present invention, in which cDNA is synthesized from a DNA probe immobilized to magnetic beads, it is not necessary to use exonuclease I. More specifically, the protocol of the present invention does not contain a degradation/removal step by a DNase reaction. Thus, the present invention has an excellent characteristic: a major cause of producing amplification bias, i.e., treatment with exonuclease I, can be avoided.

In step (3) of a poly A addition reaction (addition reaction of a polynucleotide sequence with one type of nucleotides), one type of nucleotides, for example, dATP, may be sequentially added to the 3' terminal of the first strand cDNA obtained by the reverse transcription to form a polynucleotide sequence with one type of nucleotides, for example, a poly A sequence, at the 3' terminal of the first strand cDNA. Upon that, as described in step (1), it is important to optimize the amount of DNA probe to be immobilized to magnetic beads (for example, $3\times10^3$ to $4\times10^3$ DNA molecules/magnetic bead). If such optimization is not performed, a monotype nucleotide (for example, dATP) is not only added to the 3' terminal of cDNA by the addition reaction, but also added to a free 3' terminal of DNA probe, which is immobilized to magnetic beads in step (1) without capturing mRNA. The poly A sequence (a polynucleotide sequence with one type of nucleotides) formed on the free DNA probe will serve as a template, to which a second probe is to be hybridized in a later step and will be a cause of producing an undesired artifact during PCR amplification. Actually, if the amount of DNA probe to be immobilized to magnetic beads is increased, thereby increasing the ratio of DNA probe having a free 3' terminal and thereafter PCR is performed, a large amount of PCR artifact that is hard to be removed by purification is produced, resulted in the reduction of the amplification amount of desired product.

After completion of the poly A addition (addition of one type of polynucleotides) reaction, it may be preferable to remove the solution used in the addition reaction while magnetically separating magnetic beads and wash the magnetic beads. In this step, preventing carryover of the reaction solution used in the previous step is the point, similarly to step (2). If the solution is not removed, unreacted nucleotides (for example, dATP) that are not used in the poly A addition (addition of one type of polynucleotides) reaction may be carried over in the following PCR amplification step. If so, the ratio of four types of nucleotides (dATP, dCTP, dGTP, and dTTP) to be used in PCR falls outside the proper ratio. As a result, a specific nucleotide (for example, dATP) alone is present in a large amount and a wrong nucleotide is mistakenly incorporated upon DNA synthesis, possibly introducing a mutation in the synthesized DNA or decreasing amplification efficiency.

Figure 5:
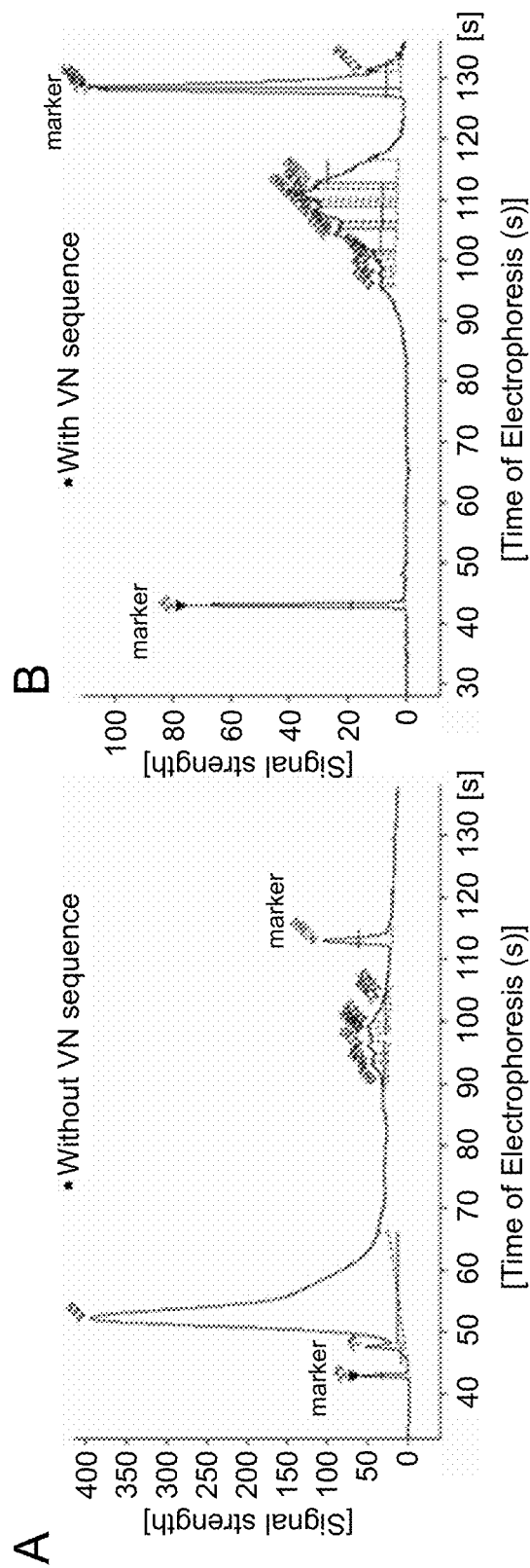
FIG. 5 is a graph showing an electrophoresis pattern of a 1st PCR product (purified by AMPure kit) obtained by amplifying a sample, which is 2nd strand cDNA synthesized using a primer having no \TN sequence or a primer having a VN sequence, as a template.

In step (4) of a second strand cDNA synthesis, a second DNA probe (No. 2) can be hybridized with the polynucleotide sequence (for example, poly A sequence), which is added to the 3' terminal of the first strand cDNA in the previous step, to perform synthesis reaction of a second strand cDNA. The second DNA probe has a second tag sequence and a complementary sequence to the polynucleotide sequence. In this step, what is the most important point is that a two-nucleotide random sequence is present at the 3' terminal of the second DNA probe. Owing to this, the amount of small artifact fragments produced by amplification can be drastically reduced (FIG. 5). As such random sequence, a VN sequence (V represents A or G or C, and N represents A or G or C or T) may be used.

In the case of a probe having no VN sequence at the 3' terminal, even if the probe is hybridized with any position of the polynucleotide sequence (for example, poly A sequence), the probe starts synthesis as long as the 3' terminal is present within the polynucleotide sequence (for example, poly A sequence). For example, in poly A addition (addition of one type of polynucleotides) reaction by terminal deoxynucleotidyl transferase (TdT) that can be employed in step (3), the length of the one type of nucleotides (for example, A) to be added to the 3' terminal of DNA may be extremely long and sometimes exceed several hundreds of bases. Accordingly, the DNA probes may be hybridized with every available sites in the long polynucleotide sequence and may start synthesis reactions from the sites. As a result, they possibly inhibit their synthesis reactions each other and produce unnecessary artifacts.

However, if a probe having a VN sequence at the 3' terminal is used, a synthesis reaction may be started only from the probe that is accurately hybridized with the border sequence between the polynucleotide sequence (for example, poly A sequence) and a cDNA sequence to efficiently synthesize a second strand cDNA having a constant length. As a result, it is possible to prevent production of unnecessary artifact.

According to the protocol of the present invention, as described particularly in step (3) above, DNA fragments having the polynucleotide sequence (for example, poly A sequence) directly added to the first DNA probe immobilized onto magnetic beads are present. In order to reduce the amount of artifact produced from these fragments as a template by amplification, as much as possible, it is very important to use the probe having a VN sequence in this step.

In the amplification step (5), a DNA amplification reaction (PCR reaction) may be performed using the second strand cDNA prepared in step (4) as a template. At this time, removing small artifact fragments produced by amplification may be the most important point in this step. Particularly, removing small artifact fragments of 200 bp or less produced by amplification from the amplified products by the 1st PCR (PCR initially performed) is important. If such small fragments remain, a large amount of small fragments (200 bp or less) may be produced by amplification in the following 2nd PCR step, in which amplification is performed using the 1st PCR product as a template, and the amount of desired amplified products having high-molecular weights extremely reduces.

In addition, it is difficult to completely remove a large amount of small fragments produced by amplification even by the following purification operation. As a result, a large amount of small artifact fragments may be carried over in a large-scale sequencing, and the quality of the sequencing drastically decreases.

In contrast, in the method of Tang et al. (Non Patent Documents 4 and 5), small artifact fragments finally produced by amplifications are removed by excising a gel after electrophoresis containing a desired high molecular weight product. However, it is difficult to accurately control the site of the gel to be excised and thus the sampling region to be excised varies depending upon the experiment. In other words, excising bias may occur.

Figure 6:
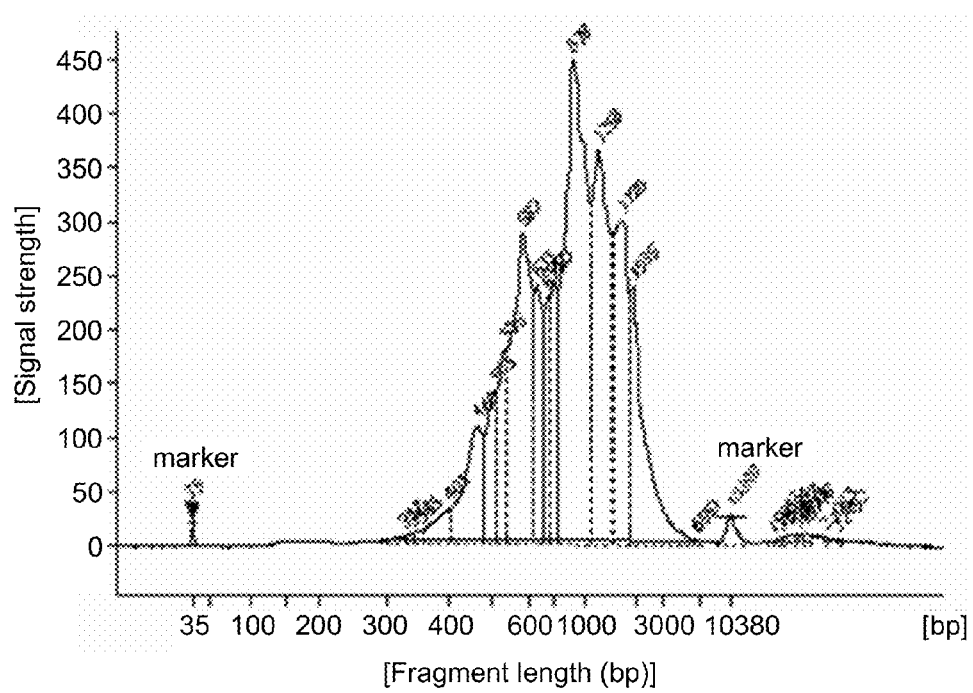
FIG. 6 is a graph showing an electrophoresis pattern of a final amplified DNA product (2nd PCR product purified) prepared from a single-cell HCT116 in accordance with the protocol of the present invention.

According to the present invention, each step is optimized to drastically reduce the amount of artifact. In this manner, the present invention enables to separate a desired product by purification utilizing adsorption of DNA to beads without excising of a gel. More specifically, for example, Agencourt AMPure (BECKMAN COULTER) can be used to adsorb DNA to beads. In this method, since an excision operation is not required, no excising bias can be produced. That is, excising bias may be overcome and small fragments (200 bp or less) may be almost completely removed by reducing artifact production during amplification in combination with employing purification based on adsorption to beads. As a result, a desired product can be successfully purified (FIG. 6).

Figure 8:
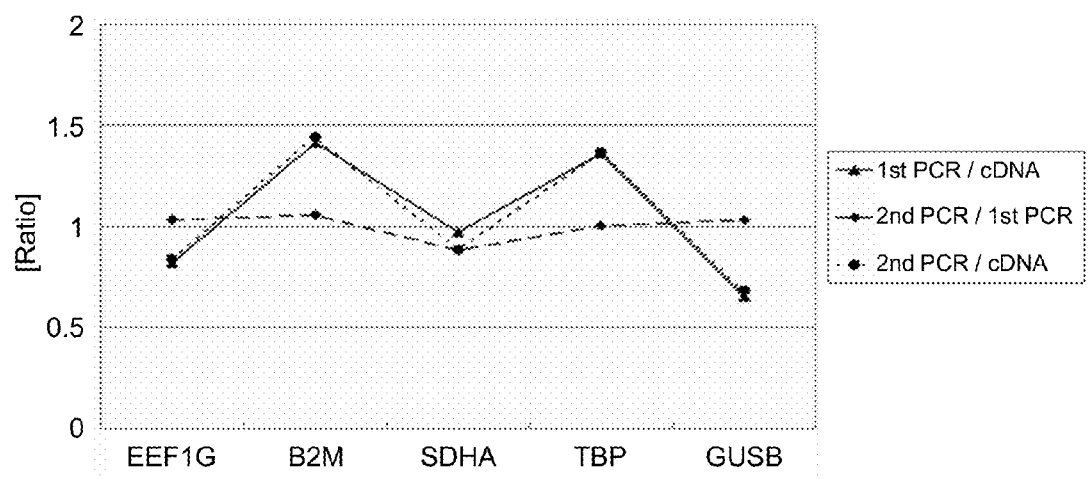
FIG. 8 is a graph showing variation of amplification rates of five genes shown in FIG. 7. The abscissa axis indicates the names of five types of genes. The vertical axis indicates the rate of the amplification rate of each gene relative to geometric mean of amplification rates of five types of genes.

Another important point in this step is setting the number of amplification reaction (PCR) cycles to the number or less at which exponential amplification initiates in order to perform amplification with less PCR bias. Efficient amplification with less bias can be achieved by dividing PCR into two stages: 1st PCR where PCR is performed using second strand cDNA immobilized to magnetic beads as a template; and 2nd PCR where PCR is performed using the 1st PCR product amplified in a solution as a template, and performing an amplification reaction by reducing the number of PCR cycles in each stage (FIG. 8). In contrast, according to the present invention, since a factor inhibiting amplification efficiency during PCR amplification is drastically removed, a desired product can be amplified in a sufficient amount (several hundreds of ng) even in 1st PCR alone with lower number of cycles (20 or less).

According to the aforementioned steps, the present invention realized a method for amplifying a sufficient amount of sample for a large-scale DNA sequencing from one or a few cells without bias. Furthermore, the present invention has the following characteristics.

In this method, since a cDNA library having cDNA fragments immobilized to magnetic beads can be prepared, the cDNA-immobilized magnetic beads can be repeatedly used as a template. The cDNA-immobilized magnetic beads bring a larger amount of amplified product since amplification can be performed multiple times; at the same time, the magnetic beads can be used for evaluation of amplification bias of the amplified product.

Usually, in preparing cDNA from a trace amount of sample such as a single cell and amplifying it, it is necessary to monitor whether the amplification process proceeds smoothly without bias. However, since the starting amount of sample taken from a single cell is extremely small, the total amount of cDNA should be used for an amplification reaction. Thus, an aliquot of cDNA cannot be taken for monitoring for determining the ratio of genes present in a cDNA library. For this reason, it is difficult to evaluate whether individual genes were amplified without bias during PCR amplification.

If magnetic beads are used, since cDNA is immobilized to the magnetic beads, it is possible to re-use the magnetic beads as a template of quantitative PCR. Owing to this, cDNA before PCR amplification and a PCR product obtained after PCR amplification can be compared and amplification bias can be evaluated.

In this method, mRNA having a poly A sequence may be captured by magnetic beads to prepare a cDNA library. Upon that, small RNA such as microRNA having no poly A sequence may not be captured by the magnetic beads and may remain in a solution. Thus, if the microRNA present in the solution is measured by quantitative PCR, the relationship of an amount of an mRNA in a single cell with comprehensive expression can be checked. Accordingly, the protocol of the present invention may include measurement of RNA having no 3' terminal-poly A sequence in the remaining solution after mRNA is captured by a solid carrier. The measurement of microRNA by PCR can be used in the case of checking suppressing effect of mRNA expression within a cell by introducing foreign siRNA into the cell.

Next, the preferable embodiments of steps in the protocol of the invention: (1) cDNA synthesis, (2) removal of a reverse transcription reaction solution, (3) poly A sequence addition (addition of a polynucleotide sequence of one type of nucleotides), (4) second strand cDNA synthesis, and (5) amplification will be more specifically described subsequently in this order.

(1) cDNA Synthesis

In this step, in addition to pretreatment for cells, four steps: separating one or a few cells, lysing a cell, capturing mRNA, and performing a reverse transcription reaction, should be considered. The term "one or a few cells" refers to 1 to 100 cells, preferably 1 to 50 cells, more preferably 1 to 20 cells, particularly 1 to 10 cells, 1 to 5 cells, 1 to 3 cells, 1 or 2 cells, and particularly a single cell. Separation of one or a few cells may be manually performed under observation of a microscope. Various pipettes for picking up a trace amount of sample such as MICRODISPENSER (Drummond) and a pico pipette (Altair Corporation) can be used. In addition, a cell(s) can be automatically picked up by using an apparatus. Various automatic cell separation apparatuses including a cell sorter are available. The cell(s) may be isolated, placed in a reaction vessel, and sequentially subjected to reactions one after another in the same vessel until a cDNA library is prepared. In this way, loss of trace-amount nucleic acid due to the adsorption is minimized. As the vessel used herein, a tube having a low nucleic-acid adsorptive property such as a MaxyClear tube (Axygen) and a Hydrophobic Microcentrifuge Tube (SSI) may be preferably used. Furthermore, it is preferable that the wall surface of a vessel be coated with a nucleic acid adsorption-preventing polymer in order to prevent nucleic acid adsorption.

For lysing cell(s), a surfactant having a cell-membrane lysis action, such as NonidetP-40 surfactant, can be used. The surfactant is used in a concentration within the range not inhibiting the following step. Furthermore, a commercially available kit containing a cell extraction reagent such as SuperScriptIII CellsDirect cDNA Synthesis System (Life technologies, hereinafter referred to as "Life") can be used.

In capturing mRNA, a probe for capturing mRNA (first DNA probe) may be used by immobilizing it to a solid carrier. Specifically, magnetic beads are the most desirable as a solid carrier; Dynabeads MyOne streptavidin C1 (diameter 1 µm, Life) is desirable; and Dynabeads M-280 and even other magnetic beads can be used. Furthermore, beads made of another material such as Sepharose beads and the inner wall of a reaction tube or membrane can be used as a solid carrier as long as a solution can be washed and removed therefrom. A DNA probe can be immobilized to a solid carrier via the 5' terminal of the probe. Immobilization is most desirably made by a binding method via biotin-avidin binding in view of strength of immobilization and its efficiency; however, other immobilization method through a covalent bond can be used. As a DNA probe, a probe having high binding ability with a nucleic acid such as LNA (Locked Nucleic Acid, Exiqon) can be used.

To the 3' terminal of a first DNA probe sequence to be immobilized, a continuous sequence of T (poly T sequence) consisting of 15 bp to 35 bp, for example 24 bp, may be added. The length of the poly T sequence can be changed in consideration of hybridization efficiency with mRNA. To the 5' side of the continuous sequence of T, a first tag sequence, which serves as a template of a primer in the following PCR amplification reaction, may be added. The first tag sequence is not particularly limited as long as it is a nucleotide sequence not present in the product to be amplified and measured; however, a sequence which will not be formed into e.g., a primer dimmer in the following PCR amplification reaction is desirable. To the 5' terminal of the probe following the tag sequence, a sequence serving as a spacer may be introduced. The spacer sequence is interposed between the probe and an immobilization carrier upon immobilization. Designing of such a tag sequence and a first probe may be well-known to those skilled in the art.

In this step, the amount of first DNA probe to be immobilized to magnetic beads may be important. The amount of DNA probe to be immobilized to magnetic beads is desirably more than about $2\times10^3$ molecules to $10^5$ molecules per magnetic bead, preferably $3\times10^3$ molecules to $10^5$ molecules and more preferably $4\times10^3$ molecules to $10^5$ molecules in consideration of efficiency of the following reverse transcription reaction. In contrast, in consideration of the following PCR amplification step, the immobilization amount is desirably about $4\times10^3$ molecules or less, since no artifact is produced during amplification. Therefore, the suitable immobilization amount in view of both the reverse transcription and PCR amplification is more than $2\times10^3$ molecules to $4\times10^3$ molecules per magnetic bead, preferably $3\times10^3$ molecules to $4\times10^3$ molecules, and more preferably $4\times10^3$ molecules. However, even if the number of molecules differs about two fold, they may be regarded as equivalent, taking measurement error of molecular number into consideration. Furthermore, the number of magnetic beads per reaction in the case of Dynabeads MyOne streptavidin C1, is desirably about $10^7$; however, magnetic beads within the range of about $10^6$ up to $10^8$ can be used. Note that the optimal amount of DNA probe to be immobilized per magnetic bead varies if a sequence, which has an effect of specifying the reverse transcription initiation point as the initiation point of a poly A sequence of mRNA, such as a VN sequence, is introduced into the 3' terminal of the DNA probe. In this case, in view of reverse transcription efficiency, the DNA-probe amount per magnetic bead is desirably $10^4$ molecules or more.

In the reverse transcription reaction, SuperScriptIII, which can mediate a reverse transcription reaction at a high temperature of 50° C., is desirably employed; however, other reverse transcriptases, such as M-MLV, can be used. Besides these, various types of RNase inhibitors, and further, a single-strand DNA binding protein such as T4 gene 32 protein (Roche) are desirably added in the reverse transcription reaction, as is known in the art.

(2) Removal of Reverse Transcription Reaction Solution

A step of removing the reverse transcription reaction solution containing a reverse transcriptase used in the previous step is essential in the present invention. The reaction solution can be removed by magnetic separation of magnetic beads. Sharp and quick separation can be achieved if NdFeB magnet is used as a magnet for magnetic separation; however, other magnets such as commercially available MPC-S magnet table (Life) can be used. Magnetic beads separated by magnetic separation may be washed with 10 mM Tris-HCl pH8.0+0.1% Tween20; however, another buffer solution can be used as long as it is suitable for dispersing magnetic beads. Furthermore, if a carrier other than magnetic beads is used, it is necessary to remove the reaction solution by another method such as centrifugal operation.

For completely removing the reverse transcription reaction solution, it is effective to allow magnetic beads to stand still in a fresh buffer solution for a while after they are separated by magnetic separation and washed. By the operation, it is presumed that components adsorbed to magnetic beads in the reverse transcription reaction solution can be removed. More specifically, a glycine buffer (67 mM Glycine-KOH, 6.7 mM $MgCl_2$, 10 mM 2-Mercaptoethanol, pH9.5) mainly containing glycine may be added to the magnetic beads after they are washed, reacted at 37° C. for 15 minutes, and further reacted at 70° C. for 10 minutes. In this manner, it is expected that efficiency of the following amplification can be increased. Other than Glycine buffer, Tris buffer can be used as the buffer to be added, and a solution such as DW (distilled water) can be used as long as the same washing effect of magnetic beads can be expected. Based on the same way of thinking, if magnetic beads are treated with e.g., a protein adsorption-preventing agent such as an MPC polymer in advance, the same effect can be expected since adsorption of components in the reverse transcription reaction solution to beads can be prevented.

(3) Addition of a Polynucleotide Sequence with One Type of Nucleotides (Addition of Poly A Sequence)

In this step, an addition reaction of a polynucleotide sequence with one type of nucleotides (addition of poly A sequence) and a degradation reaction of mRNA can be simultaneously performed. RNAaseH may be used for degradation of mRNA; whereas Terminal deoxynucleotidyl transferase (TdT), for example, may be used for adding a polynucleotide sequence with one type of nucleotides (addition of poly A sequence). As the nucleotides to be added, A (adenine) may be desirable; however, A (adenine) can be replaced with another base such as C (cytosine) or G (guanine). After the addition reaction of a polynucleotide sequence with one type of nucleotides, it is preferable that the reaction solution be removed and the magnetic beads be washed. The removal/washing may be performed using the magnetic separation reaction of magnetic beads in the same manner as shown in the above (2).

(4) Synthesis of a Second Strand cDNA (2nd Strand cDNA)

As the second DNA probe for use in synthesis of a second strand cDNA, a DNA probe, which has a second tag sequence serving as a PCR template on the 5' side, and a complementary sequence to the polynucleotide sequence (for example, a continuous T sequence complementary to poly A sequence) following the second tag sequence, and further has a 2-base random sequence at the 3' terminal, may be desirably used. As the second tag sequence, a tag sequence having a different sequence from that of a first probe (No. 1) described in the above (1) should be used. Other than the condition, the tag sequence may not be particularly limited as long as the nucleotide sequence thereof is not present in the product to be amplified and measured; however, a sequence which will not be formed into e.g., a primer dimmer in the following PCR reaction is desirable. Designing of such probe can be easily carried out by those skilled in the art by use of probe designing software, etc.

As the second probe, for example, a probe having a continuous T sequence of 24 bp added thereto can be used; however, the length of the T sequence can be changed in consideration of the hybridization efficiency with mRNA. To the second probe (No. 2), a 2-base random sequence may be preferably added to the 3' terminal. As such random sequence, for example, a VN sequence (V represents A or G or C, and N represents A or G or C or T) can be used. A probe to which a single nucleotide consisting of V sequence alone is added in place of the VN sequence, may also be applicable. On and after the step of synthesizing the second strand cDNA, it is desirable that magnetic beads serving as a template be divided and placed in separate tubes and a reaction be performed in respective tubes to disperse accumulation of replication errors during DNA synthesis. A reaction can also be performed in a single tube by adding all magnetic beads (serving as a template) in place of dividing the magnetic beads.

(5) Amplification

In this step, a DNA amplification reaction (PCR amplification reaction) can be performed using the second strand cDNA prepared on magnetic beads in the previous step, as a template. As the primer, UP1 primer having the same sequence as the first probe (No. 1) and UP2 primer having the same sequence as the second probe (No. 2) except the VN sequence, can be used. Alternatively, a primer consisting of only the first and second tag sequences of the first and second probes, can be used. Furthermore, the poly T sequence present in a primer can be shortened. In short, the DNA amplification reaction may be performed using a primer having at least a first tag sequence, or a primer containing at least a first tag sequence and a primer containing at least a second tag sequence.

In this protocol, PCR may be desirably performed in two stages (1st PCR, and 2nd PCR) in order to obtain a sufficient amount of amplified product with less bias.

1st PCR may be performed using the second strand cDNA synthesized onto magnetic beads as a template. The number of cycles in 1st PCR is set at the number of cycles or less at which PCR exponential amplification is initiated and the conditions thereof should be set so as not to produce amplification bias. If a sufficient amplification amount can be obtained only by 1st PCR, 1st PCR alone may be sufficient. Furthermore, in the 1st PCR, UP1 primer alone is used by adding it to a reaction solution. As a result, linearity of PCR amplification can be expected; however, both UP1 primer and UP2 primer can be added and used.

In the 2nd PCR, a part of a 1st PCR product may be used as a template. At this time, it is desirable to use the 1st PCR product as a template after it is purified by a spin column, etc., because the amplification efficiency of the 2nd PCR improves. The amount of 1st PCR product used as a template may be appropriately determined depending upon the degree of amplification of the 2nd PCR. Furthermore, it is necessary to set the number of cycles in 2nd PCR at the number of cycles or less at which exponential PCR amplification is initiated, in the same manner as in the 1st PCR. Furthermore, in the 2nd PCR, PCR may be performed by adding two types of primers: UP1 primer and UP2 primer. The 5' terminal of the primers used herein is desirably modified with an amino group. After amplification, the amplified DNA product should be subjected to a step of fragmentation and a step of adding an adaptor for large-scale sequence. As a result of the amino modification, an adaptor cannot be bound to the both ends of the DNA product (can be bound to fragmented sequences present therein). This is effective to prevent an unnecessary tag sequence portion from being read in a large-scale sequencing. Accordingly, as long as the binding of an adaptor in the following step can be prevented, other modification methods may be applicable.

It is necessary to remove amplified artifact products, each consisting of an undesired small fragment, from the amplified DNA product. The amplified DNA product is subjected to agarose electrophoresis and a region from about 500 bp to 3000 bp may be excised and purified. In this manner, small fragments can be removed. Alternatively, in place of electrophoresis, adsorption to beads (for example, using AgencourtAMPure) may be used to remove small fragments. This method is more preferable since excising bias produced by shift of the excision position, can be prevented. Other than these, small fragments can be removed, for example, by column. Likewise, an amplified DNA product can be purified by using such various methods in combination.

The DNA product prepared through the aforementioned five steps is thereafter subjected to processes such as fragmentation and addition of an adaptor for a sequencer so as to satisfy the specifications defined by each sequencer, and then can be used as a sample for a large-scale sequencer.

The protocol of the present invention can be simply performed by use of a kit without labor. Accordingly, the present invention provides a kit for carrying out the protocol of the present invention (hereinafter referred to also as, "the present kit"). More specifically, the invention provides a kit for amplifying cDNA from mRNA in a cell, containing a solid carrier to which a first probe containing a first tag sequence and a poly T sequence is immobilized, a means for adding a polynucleotide sequence consisting of one type of nucleotides to the 3' terminal of a cDNA sequence, a second DNA probe containing a second tag sequence and a complementary sequence to the polynucleotide sequence, and a primer containing at least the first tag sequence or a primer containing at least the first tag sequence and a primer containing at least the second tag sequence.

In the present kit, the solid carrier may be preferably magnetic beads. Furthermore, in an embodiment, a first DNA probe in an amount of $4 \times 10^3$ molecules or less per solid carrier may be immobilized. In another embodiment, a first DNA probe in an amount of more than $2 \times 10^3$ molecules to $10^5$ molecules or less per solid carrier may be immobilized. Furthermore, if a sequence, such as a VN sequence, having an effect of specifying the reverse transcription initiation point as the initiation point of a poly A sequence of mRNA is introduced to the 3' terminal of the DNA probe, the first DNA probes in an amount of $10^4$ molecules or more can be immobilized per solid carrier.

In the present kit, the one type of nucleotides may be preferably adenines (A). Furthermore, as a means for adding a polynucleotide sequence, for example, terminal deoxynucleotidyl transferase (TdT) can be used.

In the present kit, the second DNA probe is a group of probes having a 2-base random sequence following the second tag sequence and the complementary sequence to the polynucleotide sequence at the 3' terminal side. Here, the random sequence is not limited; however, a VN (V represents A or G or C, and N represents A or G or C or T) can be used.

The present kit further contains reagents to be used in the protocol of the present invention, such as, a reverse transcriptase, DNA polymerase, dNTPs, a purification means (AgencourtAMPure, etc.) using adsorption to beads, a washing buffer and a cell lysate, and an instruction for carrying out the protocol of the present invention.

The protocol of the present invention and kit as described above can be used in measurement techniques in bio-fields such as biology and biochemistry and the field of medicine such as examination and diagnosis. Measurement techniques for obtaining cell information required for gene diagnosis and designing drug targeting a single cell or several cells are included. A sample equally amplified from cDNA can be used as a sample for analyzing a sequence by a large-scale DNA sequencer.

EXAMPLES

Specific examples of embodiment of the present invention will be described below with reference to the accompanying drawings. It should be noted that these examples are merely examples for realizing the present invention and are not intended to limit the present invention.

Example 1

Preparation of a Sample for Large-Scale Sequencing from a Single Cell

In this example, an example of the protocol of the present invention will be described.

<Immobilization of Probe to Magnetic Beads>

UP1 probe (SEQ ID NO: 1) prepared by adding biotin (2 molecules) to the 5' terminal was immobilized to magnetic beads (Dynabeads MyOne Streptavidin C1; Dynal). First, 120 µL of magnetic beads (about $1.2 \times 10^9$ beads) was transferred to a 2 mL-tube (Eppendorf). To the tube, 120 µL of 1× B&W buffer (1M NaCl, 0.5 mM EDTA, 10 mM Tris-HCl pH8.0, 0.1% Tween20) was added and mixed. Subsequently, the tube was set on a magnet to separate magnetic beads toward the wall surface of the tube. After that, the supernatant was removed. To the tube, 120 µL of 1× B&W buffer was added to resuspend the magnetic beads. This operation was repeated further twice to wash magnetic beads, and a 120 magnetic beads solution was prepared.

Subsequently, 2 µL (about $4.8 \times 10^{12}$ molecules) of 4 µM UP1 probe (IDT) was added to 118 µL of 1× B&W buffer and mixed. The aliquots of 15 µL were separately taken out from the solution and sequentially added to a magnetic bead solution stirred by a vortex. UP1 probe was allowed to bind to magnetic beads while stirring the mixture by a shaker at room temperature for one hour. Subsequently, the magnetic beads were separated by a magnet and the supernatant was removed. Thereafter, 240 µL of 1× B&W buffer was added and mixed. The separation/removal operation was repeated three times to wash magnetic beads. The washing operation was similarly performed three times further with 240 µL, of a 10 mM Tris pH8.0+0.1% Tween20 solution. Finally, magnetic beads were suspended in 120 µL of a 10 mM Tris pH8.0+0.1% Tween20 solution and stored at 4° C. until use (about $4 \times 10^3$ probe molecules were immobilized per magnetic bead).

UP1 Probe:

```
                                              (SEQ ID NO: 1)
5'-dual-biotin-ATATGGATCCGGCGCGCCGTCGACTTTTTTTTTT
TTTTTTTTTTTTTT-3'.
```

<Preparation of Cell Lysis Solution>

Cell lysis solution was prepared in a 0.2 mL-low adsorption tube (Axygen) so as to obtain the following concentrations.

TABLE 1

| [Cell lysis Solution] | | | |
|---|---|---|---|
| Component | Stock Concentration | Final Concentration in RT (5 µL) | 1×Volume (µL) |
| 10×PCR buffer II (AB) | 10× | 0.9× | 0.45 |
| MgCl$_2$ (AB) | 25 mM | 1.35 mM | 0.27 |
| NonidetP-40 (Thermo) | 10% | 0.45% | 0.225 |
| DTT (Invitrogen) | 100 mM | 4.5 mM | 0.225 |

TABLE 1-continued

[Cell lysis Solution]

| Component | Stock Concentration | Final Concentration in RT (5 μL) | 1xVolume (μL) |
|---|---|---|---|
| SUPERase-In (Ambion) | 20 U/μL | 0.18 U/μL | 0.045 |
| RNase Inhibitor (Ambion) | 40 U/μL | 0.36 U/μL | 0.045 |
| dNTP mixture (GE) | 2.5 mM (each) | 0.045 mM (each) | 0.09 |
| Nuclease-free DW (Ambion) | — | — | 2.7 |
| UP1-beads[#1] | $10^7$ beads/μL | $10^7$ beads | |
| spike RNA[#2] | 100 equivalents/μL | 1 equivalent | 0.01 |
| Total | | | 4.06 |

In Table 1:
[#1]UP1-bead: 1 μL ($10^7$ beads) of UP1 probe (about 4 × $10^3$ copies) immobilized per magnetic bead is used. The probe is magnetically separated and the supernatant (1 μL) is removed, and then a cell lysis solution having a composition shown in the above table is added.
[#2]Added any time as necessary. Four types of RNA spikes 2, 3, 6 and 8 are prepared by using Array Control Spots and Spikes (Ambion) and 100 equivalents/μL stock solutions are prepared so as to contain 10, 50, 200 and 1000 copies per equivalent.

<Sampling of Single Cell>

From human colon cancer cells HCT116 (ATCC) cultured in a 25 cm²-culture flask (BD-Falcon), the culture solution (Advanced DMEM+10% FBS, Invitorogen) was removed. After the cells were washed with 3 mL of a PBS (−) solution (Invitorogen), 1 mL of 0.25% Trypsin-EDTA (Invitorogen) was added. The solution mixture was reacted at 37° C. for 2 minutes and the cells were allowed to dissociate from the bottom surface of the flask. A culture solution (4 mL) was added to the cell solution and suspended. After trypsin was inactivated, the cell solution was transferred to a 15 mL centrifuge tube and centrifuged at 100 rpm for 3 minutes. After the supernatant was removed, the cell pellet was resuspended with 1 mL of a PBS (−) solution and stored in an incubator of 37° C. until use for experiment.

The top cover of a 96-well plate (BD-Falcon) was turned upside down and a plurality of drops (100 μL) of the PBS (−) solution were prepared in recesses of the cover. The cells were serially diluted by these drops to finally prepare a drop of the cell solution having an appropriate concentration for obtaining a single cell on a low adsorptive HydroCell 6 cm dish (CellSeed).

On the stage of a microscope, ThermoPlate (CellSeed) was set such that the temperature of the plate was 37° C. On the plate, the HydroCell dish on which the drop of the cell solution was prepared was placed. A single cell was picked up by use of MICRODISPENSER (Drummond) under observation of a microscope. About 0.5 μL of a PBS (−) solution containing the single cell picked up by the operation was added to the above cell lysis solution (4.06 μL) to prepare a lysis solution in a total amount of about 4.55 μl. Subsequently, the lysis solution was centrifuged at 10000 rpm for 15 seconds, and thereafter allowed to react at 70° C. for 90 seconds to dissolve the cell and stored on ice.

<Reverse Transcription Reaction and Washing>

To the reaction solution (4.55 μL) prepared in the previous step and to which the cell was dissolved, a reverse transcription solution (0.45 μL) prepared in accordance with the following composition was added. The solution mixture (5 μL in total) was subjected to a reaction performed at 50° C. for 30 minutes and a reaction performed at 70° C. for 10 minutes. After completion of the reactions, the reaction solution was centrifuged and then allowed to stand still on ice for one minute. Subsequently, the reaction tube was allowed to be in contact with NdFeB magnet (Hitachi) to aggregate magnetic beads on the wall surface of the tube. The supernatant was removed and the tube was separated from the magnet. Thereafter, 50 μL of a 10 mM Tris pH8.0+0.1% Tween20 solution was added and mixed with magnetic beads, and then magnetically separated in the same manner as above. The operation was further repeated once more to wash the magnetic beads. Finally, the magnetic beads were mixed with 6 μL of a 10 mM Tris pH8.0+0.1% Tween20 solution.

TABLE 2

[Reverse transcription solution]

| Component | Stock Concentration | Final Concentration in RT (5 μL) | 1xVolume (μL) |
|---|---|---|---|
| Superscript III (Invitrogen) | 200 U/μL | 13.2 U/μL | 0.33 |
| RNase Inhibitor (Ambion) | 40 U/μL | 0.4 U/μL | 0.05 |
| T4 gene 32 protein (Nippon Gene) | 5 μg/μL | 0.07 μg/μL | 0.07 |
| Total | | | 0.45 |

<Reaction of Poly a Addition and Washing>

To the magnetic beads mixture solution (6 μL) prepared in the previous step, a poly A addition solution (6 μL) having the following composition was added. The solution mixture (12 μL in total) was allowed to react at 37° C. for 15 minutes to degrade RNA and add a poly A sequence to the 3' terminal of cDNA. Subsequently, the solution mixture was reacted at 70° C. for 10 minutes to inactivate the enzyme and then allowed to stand still on ice. Subsequently, the supernatant was removed with the help of magnetic separation and magnetic beads were washed with 50 μL of a 10 mM Tris pH8.0+0.1% Tween20 solution once in the same manner as above. Finally, the magnetic beads were mixed with 12 μL of a 10 mM Tris pH8.0+0.1% Tween20 solution.

TABLE 3

[Poly A addition solution]

| Component | Stock Concentration | Final Concentration (6 μL) | 1xVolume (μL) |
|---|---|---|---|
| 10xPCR buffer II | 10x | 1x | 0.6 |
| MgCl$_2$ | 25 mM | 1.5 mM | 0.36 |
| dATP (GE) | 100 mM | 3 mM | 0.18 |
| RNaseH (Invitrogen) | 2 U | 0.1 U/μL | 0.3 |
| Terminal Transferase (Invitrogen) | 15 U/μL | 0.75 U/μL | 0.3 |
| Nuclease-free DW | — | — | 4.26 |
| Total | | | 6 |

<Synthesis of 2nd Strand cDNA>

From the magnetic bead mixture solution (12 μL) prepared in the previous step, an aliquot of 3 μL was taken and added to the following 2nd strand cDNA synthesis solution (19 μL) (prepared in a 0.2 mL low adsorption tube) and the total amount was prepared to be 22 μL. The remaining magnetic bead mixture solution (remaining amount: 9 μL) was similarly added to the 2nd strand cDNA synthesis solution in an amount of 3 μL. In this manner, in total, four tubes containing the sample solution were prepared. These four tubes were subjected to a reaction at 95° C. for 3 minutes, a reaction at 44° C. for 2 minutes, and a reaction at 72° C. for 6 minutes, and then allowed to stand still at 4° C.

TABLE 4

[2nd strand cDNA synthesis solution]

| Component | Stock Concentration | Final Concentration (19 μL) | 1×Volume (μL) |
|---|---|---|---|
| 10×Ex Taq buffer (TaKaRa) | 10× | 1× | 1.9 |
| dNTPs (TaKaRa) | 2.5 mM | 0.25 mM | 1.9 |
| UP2-VN probe (Sigma) | 100 μM | 0.3 μM | 0.057 |
| ExTaq HS (TaKaRa) | 5 U/μL | 0.05 U/μL | 0.19 |
| Nuclease-free DW | — | — | 14.953 |
| Total | | | 19 |

UP2-VN Probe:

(SEQ ID NO: 2)
5'-ATATCTCGAGGGCGCGCCGGATCCTTTTTTTTTTTTTTTTTTTT
TTVN-3'

[wherein, V represents A or G or C, and N represents A or G or C or T].

<1st PCR Amplification and Purification>

To the reaction solution (22 μL) prepared in the previous step and in which the 2nd strand cDNA synthesis was completed, 1st PCR reaction solution (19 μL) shown below was added to prepare a solution mixture (41 μL in total). The mixing was performed in all the four tubes. The four tubes in which the solution mixture was prepared were allowed to react at 95° C. for 3 minutes and thereafter subjected to a cycle consisting of a reaction at 95° C. for 30 seconds, a reaction at 67° C. for one minute and a reaction at 72° C. for 6 minutes (+6 seconds per cycle). The cycle was repeated 20 times and the reaction products were stored at 4° C.

The amplified PCR product obtained above was purified by use of Agencourt AMPure XP kit (Beckman Coulter, Inc.). To four PCR products (each 414) of 164 μL, 0.6 volumes of AMPureXP reagent (98.4 μL), which is a condition for removing fragments of 200 bp or less, specified by the AMPure XP kit, was mixed. Purification was performed in accordance with the instruction book attached to the kit to finally obtain an eluate (50 μL).

TABLE 5

[1st PCR reaction solution]

| Component | Stock Concentration | Final Concentration (19 μL) | 1×Volume (μL) |
|---|---|---|---|
| 10×Ex Taq buffer | 10× | 1× | 1.9 |
| dNTPs | 2.5 mM | 0.25 mM | 1.9 |
| UP1 primer (Sigma) | 100 μM | 2.2 μM | 0.418 |
| ExTaq HS | 5 U/μL | 0.04 U/μL | 0.19 |
| Nuclease-free DW | — | — | 14.592 |
| Total | | | 19 |

UP1 Primer:

(SEQ ID NO: 3)
5'-ATATGGATCCGGCGCGCCGTCGACTTTTTTTTTTTTTTTTTTTT
TT-3'.

<2nd PCR Amplification>

Of the purified 1st PCR product solution (50 μL) prepared in the previous step, 1 μL was taken and used to prepare a 2nd PCR reaction solution shown below in four tubes. Subsequently, the solutions were allowed to react at 95° C. for 3 minutes, and thereafter subjected to a cycle consisting of a reaction at 95° C. for 30 seconds, a reaction at 67° C. for one minute and a reaction at 72° C. for 6 minutes (+6 seconds per cycle). The cycle was repeated 15 times and the reaction products were stored at 4° C.

TABLE 6

[2nd PCR reaction solution]

| Component | Stock Concentration | Final Concentration (50 μL) | 1×Volume (μL) |
|---|---|---|---|
| purified 1st PCR product | — | — | 1 |
| 10×Ex Taq buffer | 10× | 1× | 5 |
| dNTPs | 2.5 mM | 0.25 mM | 5 |
| Amine-UP1 primer (Sigma) | 100 μM | 1 μM | 0.5 |
| Amine-UP2 primer (Sigma) | 100 μM | 1 μM | 0.5 |
| ExTaq HS | 5 U/μL | 0.05 U/μL | 0.5 |
| Nuclease-free DW | — | — | 37.5 |
| Total | | | 50 |

Amine-UP1 Primer:

(SEQ ID NO: 4)
5'-NH$_2$-ATATGGATCCGGCGCGCCGTCGACTTTTTTTTTTTTTTTTTTTT
TTTTT-3'

Amine-UP2 Primer:

(SEQ ID NO: 5)
5'-NH$_2$-ATATCTCGAGGGCGCGCCGGATCCTTTTTTTTTTTTTTTTTTTT
TTTTT-3'.

<Purification of 2nd PCR Product>

The 2nd PCR product prepared above was purified by use of Agencourt AMPure XP kit. To four PCR products (50 μL×4=200 4), 0.6× volumes of AMPureXP reagent (120 μL), which is a condition for removing fragments of 200 bp or less, specified by the AMPure XP kit, was mixed. Purification was performed in accordance with the instruction book attached to the kit to finally obtain an eluate (50 μL).

Subsequently, the eluate (50 μL) was purified by a PCR purification kit (JENA) in accordance with the instruction book attached to the kit to finally obtain a DNA fragment solution (about 50 μL). DNA fragment (1 μL) was taken and analyzed by a bio-analyzer electrophoresis apparatus (Agilent). The electrophoresis pattern of the final amplified DNA product (purified 2nd PCR product) prepared from a single cell of HCT116 is shown in FIG. 6. As a result, it was found that low molecular artifact fragments are removed and a desired product to be used as a large-scale sequencer sample (FIG. 6) is obtained. Furthermore, the DNA amount of final purified product was measured. As a result, it was found that a DNA fragment of about 700 ng to 1200 ng is obtained.

Example 2

Evaluation of Amplification Efficiency and Amplification Bias

To evaluate amplification efficiency of DNA and amplification bias in each step of the protocol shown in Example 1, the amount of each gene was measured by a quantitative PCR method. Quantitative measurement was performed by use of 7900HT Fast Real-Time PCR system apparatus manufactured by Applied Biosystems. First, cDNA library was prepared from a single cell of HCT116 in accordance with the protocol of Example 1 and the amounts of cDNA of five types of genes (EEF1G, B2M, SDHA, TBP, and GUSB) were measured. As the quantitative PCR of these five types of genes, a TaqMan Probe method using an MGB fluorescent probe was employed. MGB fluorescent probes and PCR primers for individual genes are shown in the following SEQ ID NOs: 6 to 20. As a reaction reagent of the quantitative PCR, Premix Ex Taq (Takara Bio Inc.) was used. The reaction reagent was prepared in accordance with the manual attached. The amount of each cDNA was determined by an absolute quantitative method using the calibration curve prepared from a standard DNA sample.

Primer Sequences:

```
EEF1G qPCR-F:
                                (SEQ ID NO: 6)
5'-TTTCCGCTGAGTCCAGATT-3'

EEF1G qPCR-R:
                                (SEQ ID NO: 7)
5'-CCCTGATTGAAGGCTTTG-3'

EEF1G MGB Probe:
                                (SEQ ID NO: 8)
5'-FAM-TGGACTACGAGTCATACACA-MGB-3'

B2M qPCR-F:
                                (SEQ ID NO: 9)
5'-GCATCATGGAGGTTTGAAG-3'

B2M qPCR-R:
                                (SEQ ID NO: 10)
5'-TATAACCCTACATTTTGTGCAT-3'

B2M MGB Probe:
                                (SEQ ID NO: 11)
5'-FAM-CGCATTTGGATTGGATGA-MGB-3'

SDHA qPCR-F:
                                (SEQ ID NO: 12)
5'-CACTGGGAAGGTCACTCTG-3'

SDHA qPCR-R:
                                (SEQ ID NO: 13)
5'-TTCTGTCATCACCACATCTTG-3'

SDHA MGB Probe:
                                (SEQ ID NO: 14)
5'-FAM-CCATTCGCTCCTACTGAT-MGB-3'

TBP qPCR-F:
                                (SEQ ID NO: 15)
5'-ACCCACCAACAATTTAGTAGTTAT-3'

TBP qPCR-R:
                                (SEQ ID NO: 16)
5'-GCTCTGACTTTAGCACCTGTTA-3'

TBP MGB Probe:
                                (SEQ ID NO: 17)
5'-FAM-AGCCAGAGTTATTTCCTGG-MGB-3'

GUSB qPCR-F:
                                (SEQ ID NO: 18)
5'-TGAACAGTCACCGACGAGAG-3'

GUSB qPCR-R:
                                (SEQ ID NO: 19)
5'-TCCAAACATTGTGACTTGGCTAC-3'

GUSB MGB Probe:
                                (SEQ ID NO: 20)
5'-FAM-CAGCGTTCCTTTTGCGAG-MGB-3'.
```

Subsequently, a cDNA library was prepared from a single cell of HCT116 in the same manner as above and subjected to the reaction steps of 1st PCR and 2nd PCR. These 1st PCR products and 2nd PCR products were subjected to quantitative PCR in the same manner as above and the DNA amounts of each of the five types of genes was measured.

Figure 7:
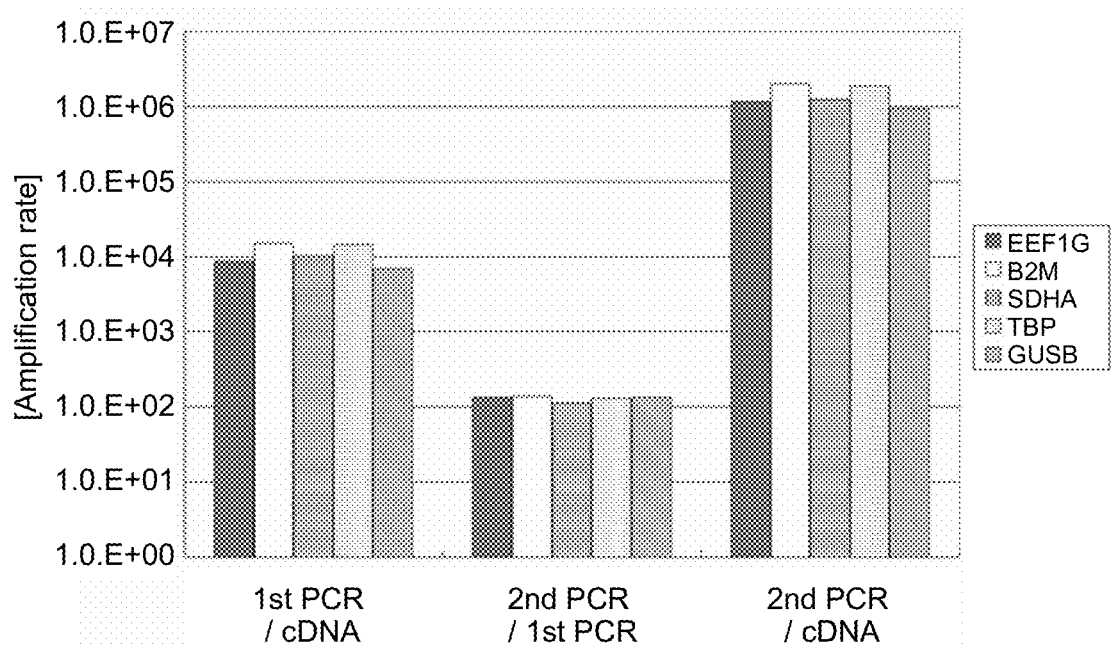
FIG. 7 is a graph showing DNA amplification rate between individual steps. The vertical axis indicates DNA amplification rate. In the abscissa axis, 1st PCR/cDNA indicates the amplification rate of a 1st PCR relative to cDNA; 2nd PCR/1st PCR indicates the amplification rate of 2nd PCR relative to 1st PCR; and 2nd PCR/cDNA indicates the amplification rate of 2nd PCR relative to cDNA. The amplification rates were measured with respect to five types of genes (EEF1G, B2M, SDHA, TBP, GUSB).

FIG. 7 shows amplification rates (1st PCR/cDNA) of 1st PCR to cDNA, amplification rates (2nd PCR/1st PCR) of 2nd PCR to 1st PCR, and amplification rates (2nd PCR/cDNA) of 2nd PCR to cDNA of five types of genes. As the amount of cDNA, an average value of those of five samples was used. As each of the amounts of 1st PCR and 2nd PCR, an average value of those of three samples was used. As a result, it was confirmed that there is no significant difference in the amplification rate among five genes (EEF1G, B2M, SDHA, TBP, and GUSB).

FIG. 8 shows how many times larger the ratio of the amplification rate of each gene relative to the geometric mean of five-gene amplification rates. This is provided to evaluate variation in amplification rate among the five genes. As a result, even in the case of the amplification rate (2nd PCR/cDNA) of 2nd PCR to cDNA, which presumably has the largest variation in amplification, the ratio of the amplification rate falls within the range of 0.5 fold to 1.5 fold. It was demonstrated that a method extremely low in amplification bias is provided by the protocol of the present invention.

Example 3

Optimization of the Amount of Probe to be Immobilized to Magnetic Beads

To optimize the amount of UP1 probe to be bound onto magnetic beads for capturing mRNA, magnetic beads were prepared by varying the amount of UP1 probe to be immobilized, and reverse transcription efficiency and cDNA amplification efficiency were determined.

According to the method described in Example 1, UP1 probe was immobilized to magnetic beads via a biotin-avidin bond. At this time, as the amount of UP1 probe to be reacted with the magnetic beads, four different amounts: 200 pmol (about $1.2 \times 10^{14}$ molecules), 20 pmol, 8 pmol and 4 pmol, were used. If the UP1 probe is subjected to the reaction in these amounts, it is calculated that UP1 probe of $1 \times 10^5$, $1 \times 10^4$, $4 \times 10^3$, and $2 \times 10^3$ molecules are to be immobilized per magnetic bead, respectively. Then, mRNA (2 pg) was captured by use of these four samples of UP1 probes immobilized magnetic beads ($10^7$ beads) and subjected to a reverse transcription reaction. The mount of EEF1G gene present on the magnetic beads was determined by a quantitative PCR method (FIG. 2A). As a result, it was found that reverse transcription amounts did not change within the range of a probe amount from $1 \times 10^5$ to $4 \times 10^3$ molecules/bead; however, if the immobilization amount is reduced to $2 \times 10^3$ molecules/bead, the reverse transcription amount reduces. From this, it was found that the amount of probe to be used is preferably more than $2 \times 10^3$ molecules per bead, for example, $3 \times 10^3$ molecules or more.

Using DNA probe (UP1-VN probe) prepared by introducing a VN sequence at the 3' terminal of UP1 probe, an optimal immobilization amount to magnetic beads was obtained (FIG. 9) in the same manner. The experiment was performed using three types of genes (EEF1G, B2M, and TBP). As a result, it was found that a high reverse transcription efficiency is obtained if the UP1VN probe is immobilized in a ratio of $10^4$ molecules or more per magnetic bead.

UP1-VN Probe (SEQ ID NO: 21)
5'-dual-biotin-ATATGGATCCGGCGCGCCGTCGACTTTTTTTTT
TTTTTTTTTTTTTTVN-3'

[wherein, V represents A or G or C, and N represents A or G or C or T.]

Subsequently, samples captured by $1\times10^5$, $1\times10^4$, or $4\times10^3$ molecules/beads, in which no reduction in reverse transcription amount was observed, were subjected to up to 2nd PCR in accordance with the method of Example 1 to obtain amplified products. The amounts of EEF1G gene contained in these amplified products were determined by a quantitative PCR method and amplification efficiencies were evaluated (FIG. 2B). As a result, in the PCR product of a sample captured by probes ($1\times10^5$ molecules/bead), which are immobilized in the largest amount onto magnetic beads, the amplification amount of EEF1G gene was the lowest; conversely, in the PCR product of a sample captured by probes ($4\times10^3$ molecules/bead), which are immobilized in the smallest amount, the amplification amount was the highest.

Example 4

Verification of Effect of Reverse Transcription Reaction Solution Carried Over in the Following Step A reverse transcription reaction solution may be carried over in the following step by skipping the removal/washing operation of the reverse transcription reaction solution in the protocol of Example 1. In this case, what effect is produced was investigated. mRNA (2 pg) was subjected to the operation up to the step of a reverse transcription reaction in accordance with the method described in Example 1. Thereafter, some of the samples were subjected to a normal operation including a removal/washing step of the reverse transcription reaction solution; whereas the other samples were subjected to an operation including no removal/washing step. Both samples were subjected to the following poly A addition reaction and amplification in 1st PCR in the same manner as in the protocol. Then, the amounts of EEF1G gene at the time of reverse transcription and at the time of 1st PCR of each of the conditions (with or without washing step) were determined by a real-time PCR method, and DNA amplification amounts were compared.

As a result, it was found that the amplification amount of EEF1G gene by 1st PCR with respect to the sample which was not subjected to removal of reverse transcription reaction solution is drastically reduced compared to the sample subjected to the removal (FIG. 3).

Example 5

Verification of Effect of Exonuclease I Treatment on PCR Amplification Reaction

To check the effect of use of exonuclease I in the previous step on the following PCR amplification reaction step, a treatment with exonuclease I was performed in a step of removing an unreacted reverse transcription probe and the efficiency of the following PCR amplification was checked.

In the protocol described in Example 1, a reverse transcription reaction was performed by using free UP1 probe for reverse transcription without being immobilized to magnetic beads. As a template for the reverse transcription, mRNA (20 pg) derived from HCT116 was used. After completion of the reverse transcription, 1 μL of exonuclease I (0.5 U/4) was added to a reverse transcription reaction solution (5 μL), and a reaction was performed at 37° C. for 30 minutes. The resultant was treated at 80° C. for 25 minutes to inactivate exonuclease I and then the reaction solution was continuously subjected to general RNA degradation, poly A addition reaction and 1st PCR steps shown in Example 1. Furthermore, the amounts of four types of genes (EEF1G, B2M, TBP, and SDHA) contained in the sample immediately after completion of the reverse transcription and before addition of exonuclease I and the sample after addition of exonuclease I and completion of 1st PCR, were measured by quantitative PCR method.

The relative amounts of the remaining three types of genes were obtained based on the amount of EEF1G regarded as 100%. FIG. 4 shows the relative amounts at the time of reverse transcription and at the time of 1st PCR amplification after completion of a treatment with the exonuclease. In FIG. 4, the vertical axis indicates the relative amplification amount of each gene, which is obtained based on the amplification amount of EEF1G gene measured in the same experiment as 100%. As a result, in the case of B2M gene treated with exonuclease I, the amplification rate at the time of 1st PCR greatly decreases, compared to those of other genes, suggesting a possibility that amplification bias is produced by the treatment with exonuclease I.

Example 6

Verification of Protocol Using a Probe to which a VN Sequence is Added

Using UP2-VN probe, which was prepared by adding a 2-base VN sequence to the 3' terminal of UP2 probe (No. 2), 2nd strand cDNA was synthesized, and the effect of the VN sequence on the following PCR amplification was checked. In the step of the 2nd strand PCR synthesis shown in Example 1, 2nd strand cDNA was synthesized by using UP2-VN probe (SEQ ID NO: 2) having the VN sequence or UP2 probe (SEQ ID NO: 21) (Sigma) having no VN sequence. Finally, an amplified product by 1st PCR was obtained. The PCR products amplified were purified by use of Agencourt AMPure XP shown in Example 1. An aliquot of the purified PCR product was taken and electrophoretically analyzed by a bio-analyzer (Agilent) to check distribution of the amplified products.

In a product amplified by use of the probe having no VN sequence (FIG. 5A), a large amount of small artifact fragments near about 100 bp (electrophoresis time: about 50 to 60 s) remained without being removed. In contrast, in the case of using a probe having a VN sequence (FIG. 5B), it was found that small fragments around 100 bp are completely removed and only desired fragments of a higher molecular weight can be collected.

UP2 Probe:

(SEQ ID NO: 22)
5'-ATATCTCGAGGGCGCGCCGGATCCTTTTTTTTTTTTTTTTTTTT
TTT-3'.

Note that the present invention is not limited by the above Examples and includes various modifications. In the aforementioned Examples, for example, the present invention is described in detail so as to easily understand the invention and is not necessarily limited to a case having all constitutions described herein. Furthermore, a part of the constitution of a certain Example can be replaced with the constitution of another Example. Alternatively, the constitution of an Example may be added to the constitution of another Example. Moreover, another constitution may be added to, deleted from and substituted for a part of the constitution of an Example.

All publications, patents and patent applications cited in the present specification are incorporated herein in their entirety by reference.

Sequence Listing Free Text

SEQ ID NOs: 1 to 22: Artificial sequence (synthesized DNA)

The invention claimed is:

1. A method for amplifying cDNA from mRNA in a cell, comprising:
   (1) capturing mRNA derived from the cell by a first DNA probe comprising a first tag sequence and a poly T sequence and being immobilized to a solid carrier in a single reaction vessel, and synthesizing a first strand cDNA from the mRNA by a reverse transcription reaction;
   (2) removing a reaction reagent from the reaction vessel while keeping the first strand cDNA synthesized onto the solid carrier in the reaction vessel;
   (3) adding a polynucleotide sequence consisting of one type of nucleotides to 3' terminal of the first strand cDNA on the solid carrier;
   (4) hybridizing a second DNA probe comprising a second tag sequence and a complementary sequence to the polynucleotide sequence with the cDNA to which the polynucleotide sequence is added, and synthesizing a second strand cDNA without a degradation and removal of the first DNA probe by a DNase reaction; and
   (5) performing a DNA amplification reaction using the second strand cDNA synthesized on the solid carrier as a template.

2. The method of claim 1, wherein the solid carrier is a magnetic bead.

3. The method of claim 2, wherein, in step (1), the first DNA probe is used in an amount of $4 \times 10^3$ molecules or less per solid carrier.

4. The method of claim 2, wherein, in step (1), the first DNA, probe is used in an amount of more than $2 \times 10^3$ molecules and $10^5$ molecules or less per solid carrier.

5. The method of claim 1, wherein, in step (1), the first DNA probe is a group of probes comprising a two-nucleotide random sequence at the 3' terminal following the first tag sequence and the poly T sequence, and the first DNA probe is used in an amount of $10^4$ molecules or more per solid carrier.

6. The method of claim 1, wherein, in step (2), the reaction reagent to be removed comprises a reverse transcriptase.

7. The method of claim 1, wherein, in step (3), the nucleotides are adenines (A).

8. The method of claim 1, further comprising removing the reaction reagent after the polynucleotide sequence addition reaction of step (3).

9. The method of claim 1, wherein, in step (4), the second DNA probe is a group of probes comprising a two-nucleotide random sequence at the 3' terminal following the second tag sequence and the complementary sequence to the polynucleotide sequence.

10. The method of claim 1, wherein, in step (5), the DNA amplification reaction is performed by using the first tag sequence present at the end of the second strand cDNA synthesized on the solid carrier, or the first tag sequence and the second tag sequence.

11. The method of claim 1, wherein, in step (5), the number of amplification reaction cycles is limited to the number or less at which exponential amplification is maintained.

12. The method of claim 1, further comprising separating and removing DNA products of 200 bp or less from amplified DNA products by a method for separating and purifying the DNA products based on adsorption of DNA to beads.

13. The method of claim 1, wherein the DNA amplification reaction is performed by repeatedly using the solid carrier to which the first strand DNA is immobilized.

14. The method of claim 1, further comprising allowing the solid carrier to stand still in a fresh buffer solution, after the reaction reagent is removed, in step (2).

15. A method for determining the amount of mRNA in a cell, comprising determining the amount of mRNA in a cell based on the amount of DNA product amplified by the method of claim 1.

16. The method of claim 1, wherein the DNase reaction is an Exonuclease reaction.

\* \* \* \* \*

SEQUENCE LISTING

```
<160> NUMBER OF SEQ ID NOS: 22

<210> SEQ ID NO 1
<211> LENGTH: 48
<212> TYPE: DNA
<213> ORGANISM: Artificial
<220> FEATURE:
<223> OTHER INFORMATION: Synthetic DNA

<400> SEQUENCE: 1
atatggatcc ggcgcgccgt cgactttttt tttttttttt tttttttt          48

<210> SEQ ID NO 2
<211> LENGTH: 50
<212> TYPE: DNA
<213> ORGANISM: Artificial
<220> FEATURE:
<223> OTHER INFORMATION: Synthetic DNA
<220> FEATURE:
<221> NAME/KEY: misc_feature
<222> LOCATION: (50)..(50)
<223> OTHER INFORMATION: n is a, c, g, or t

<400> SEQUENCE: 2
atatctcgag ggcgcgccgg atccttttt tttttttttt ttttttttvn          50

<210> SEQ ID NO 3
<211> LENGTH: 48
<212> TYPE: DNA
<213> ORGANISM: Artificial
<220> FEATURE:
<223> OTHER INFORMATION: Synthetic DNA

<400> SEQUENCE: 3
atatggatcc ggcgcgccgt cgactttttt tttttttttt tttttttt          48

<210> SEQ ID NO 4
<211> LENGTH: 48
<212> TYPE: DNA
<213> ORGANISM: Artificial
<220> FEATURE:
<223> OTHER INFORMATION: Synthetic DNA

<400> SEQUENCE: 4
atatggatcc ggcgcgccgt cgactttttt tttttttttt tttttttt          48

<210> SEQ ID NO 5
<211> LENGTH: 48
<212> TYPE: DNA
<213> ORGANISM: Artificial
<220> FEATURE:
<223> OTHER INFORMATION: Synthetic DNA

<400> SEQUENCE: 5
atatctcgag ggcgcgccgg atccttttt tttttttttt tttttttt          48

<210> SEQ ID NO 6
<211> LENGTH: 19
<212> TYPE: DNA
```

<213> ORGANISM: Artificial
<220> FEATURE:
<223> OTHER INFORMATION: Synthetic DNA

<400> SEQUENCE: 6
tttccgctga gtccagatt                                             19

<210> SEQ ID NO 7
<211> LENGTH: 18
<212> TYPE: DNA
<213> ORGANISM: Artificial
<220> FEATURE:
<223> OTHER INFORMATION: Synthetic DNA

<400> SEQUENCE: 7
ccctgattga aggctttg                                              18

<210> SEQ ID NO 8
<211> LENGTH: 20
<212> TYPE: DNA
<213> ORGANISM: Artificial
<220> FEATURE:
<223> OTHER INFORMATION: Synthetic DNA

<400> SEQUENCE: 8
tggactacga gtcatacaca                                            20

<210> SEQ ID NO 9
<211> LENGTH: 19
<212> TYPE: DNA
<213> ORGANISM: Artificial
<220> FEATURE:
<223> OTHER INFORMATION: Synthetic DNA

<400> SEQUENCE: 9
gcatcatgga ggtttgaag                                             19

<210> SEQ ID NO 10
<211> LENGTH: 22
<212> TYPE: DNA
<213> ORGANISM: Artificial
<220> FEATURE:
<223> OTHER INFORMATION: Synthetic DNA

<400> SEQUENCE: 10
tataacccta cattttgtgc at                                         22

<210> SEQ ID NO 11
<211> LENGTH: 18
<212> TYPE: DNA
<213> ORGANISM: Artificial
<220> FEATURE:
<223> OTHER INFORMATION: Synthetic DNA

<400> SEQUENCE: 11
cgcatttgga ttggatga                                              18

<210> SEQ ID NO 12
<211> LENGTH: 19
<212> TYPE: DNA
<213> ORGANISM: Artificial
<220> FEATURE:
<223> OTHER INFORMATION: Synthetic DNA

<400> SEQUENCE: 12
cactgggaag gtcactctg                                             19

<210> SEQ ID NO 13
<211> LENGTH: 21
<212> TYPE: DNA
<213> ORGANISM: Artificial
<220> FEATURE:
<223> OTHER INFORMATION: Synthetic DNA

<400> SEQUENCE: 13
ttctgtcatc accacatctt g                                              21

<210> SEQ ID NO 14
<211> LENGTH: 18
<212> TYPE: DNA
<213> ORGANISM: Artificial
<220> FEATURE:
<223> OTHER INFORMATION: Synthetic DNA

<400> SEQUENCE: 14
ccattcgctc ctactgat                                                  18

<210> SEQ ID NO 15
<211> LENGTH: 24
<212> TYPE: DNA
<213> ORGANISM: Artificial
<220> FEATURE:
<223> OTHER INFORMATION: Synthetic DNA

<400> SEQUENCE: 15
acccaccaac aatttagtag ttat                                           24

<210> SEQ ID NO 16
<211> LENGTH: 22
<212> TYPE: DNA
<213> ORGANISM: Artificial
<220> FEATURE:
<223> OTHER INFORMATION: Synthetic DNA

<400> SEQUENCE: 16
gctctgactt tagcacctgt ta                                             22

<210> SEQ ID NO 17
<211> LENGTH: 19
<212> TYPE: DNA
<213> ORGANISM: Artificial
<220> FEATURE:
<223> OTHER INFORMATION: Synthetic DNA

<400> SEQUENCE: 17
agccagagtt atttcctgg                                                 19

<210> SEQ ID NO 18
<211> LENGTH: 20
<212> TYPE: DNA
<213> ORGANISM: Artificial
<220> FEATURE:
<223> OTHER INFORMATION: Synthetic DNA

<400> SEQUENCE: 18
tgaacagtca ccgacgagag                                                20

<210> SEQ ID NO 19
<211> LENGTH: 23
<212> TYPE: DNA
<213> ORGANISM: Artificial
<220> FEATURE:

```
<223> OTHER INFORMATION: Synthetic DNA

<400> SEQUENCE: 19
tccaaacatt gtgacttggc tac                                          23

<210> SEQ ID NO 20
<211> LENGTH: 18
<212> TYPE: DNA
<213> ORGANISM: Artificial
<220> FEATURE:
<223> OTHER INFORMATION: Synthetic DNA

<400> SEQUENCE: 20
cagcgttcct tttgcgag                                                18

<210> SEQ ID NO 21
<211> LENGTH: 50
<212> TYPE: DNA
<213> ORGANISM: Artificial
<220> FEATURE:
<223> OTHER INFORMATION: Synthetic DNA
<220> FEATURE:
<221> NAME/KEY: misc_feature
<222> LOCATION: (50)..(50)
<223> OTHER INFORMATION: n is a, c, g, or t

<400> SEQUENCE: 21
atatggatcc ggcgcgccgt cgactttttt tttttttttt tttttttvn              50

<210> SEQ ID NO 22
<211> LENGTH: 48
<212> TYPE: DNA
<213> ORGANISM: Artificial
<220> FEATURE:
<223> OTHER INFORMATION: Synthetic DNA

<400> SEQUENCE: 22
atatctcgag ggcgcgccgg atccttttt tttttttttt tttttttt                48
```